United States Patent
Reith et al.

(10) Patent No.: US 11,135,771 B1
(45) Date of Patent: Oct. 5, 2021

(54) SYSTEM AND METHOD OF MANUFACTURING A MEDICAL IMPLANT

(71) Applicant: Curiteva, Inc., Tanner, AL (US)

(72) Inventors: Todd Reith, West Chester, PA (US); Eric Linder, Dublin, OH (US); Ryan Heskett, Wellington, FL (US)

(73) Assignee: Curiteva, Inc., Tanner, AL (US)

( * ) Notice: Subject to any disclaimer, the term of this patent is extended or adjusted under 35 U.S.C. 154(b) by 0 days.

(21) Appl. No.: 17/226,200

(22) Filed: Apr. 9, 2021

(51) Int. Cl.
| | |
|---|---|
| *B29C 64/245* | (2017.01) |
| *A61F 2/30* | (2006.01) |
| *B33Y 10/00* | (2015.01) |
| *B33Y 30/00* | (2015.01) |
| *B29C 64/118* | (2017.01) |
| *B29C 64/295* | (2017.01) |
| *B33Y 80/00* | (2015.01) |
| *B33Y 50/02* | (2015.01) |
| *B29C 64/393* | (2017.01) |

(Continued)

(52) U.S. Cl.
CPC .......... *B29C 64/245* (2017.08); *A61F 2/3094* (2013.01); *B29C 64/118* (2017.08); *B29C 64/295* (2017.08); *B33Y 10/00* (2014.12); *B33Y 30/00* (2014.12); *A61F 2/4455* (2013.01); *A61F 2002/30985* (2013.01); *B29C 64/393* (2017.08); *B29K 2101/12* (2013.01); *B29L 2031/753* (2013.01); *B33Y 50/02* (2014.12); *B33Y 80/00* (2014.12)

(58) Field of Classification Search
CPC ... B29C 64/245; B29C 64/118; B29C 64/209; B22F 3/105; B23K 26/082
See application file for complete search history.

(56) References Cited

U.S. PATENT DOCUMENTS

| | | |
|---|---|---|
| 9,193,110 B2 | 11/2015 | Pridoehl et al. |
| 9,250,620 B2 | 2/2016 | Kotlus |

(Continued)

FOREIGN PATENT DOCUMENTS

| | | |
|---|---|---|
| CN | 108215194 A | 6/2018 |
| EP | 3436503 B1 | 2/2020 |
| WO | 2019/068581 A1 | 4/2019 |

OTHER PUBLICATIONS

3D Printed Peek Bone Mesh; Artstor; University of Pennsylvania Fisher Fine Arts Library Material Collection; https://library.artstor.org/#/public/27529255; Retrieved May 4, 2021.

(Continued)

*Primary Examiner* — Dah-Wei D. Yuan
*Assistant Examiner* — Andrew J Bowman
(74) *Attorney, Agent, or Firm* — Erise IP, P.A.

(57) ABSTRACT

A system and method for forming a medical implant using a printing device. The printing device includes a print head having a heated nozzle, a heated build plate for receiving the printed material thereon, and a reflective plate having an active heater. A method for forming a medical device includes extruding a printing material by contiguous deposition to form a porous object having a lattice-like structure. The medical device, such as a spinal implant, may have interconnected pores and different regions, each having a different porosity for encouraging bone growth therein. The printed medical implant may be designed to be patient-specific, customized, and printed on-demand.

20 Claims, 22 Drawing Sheets

(51) Int. Cl.
  *B29K 101/12* (2006.01)
  *B29L 31/00* (2006.01)
  *A61F 2/44* (2006.01)

(56) References Cited

U.S. PATENT DOCUMENTS

| | | | |
|---|---|---|---|
| 9,433,969 | B2 | 9/2016 | Pridoehl et al. |
| 9,527,242 | B2 | 12/2016 | Rodgers et al. |
| 9,925,714 | B2 | 3/2018 | Rodgers et al. |
| 10,189,210 | B2 | 1/2019 | Rodgers et al. |
| 10,335,856 | B2 | 7/2019 | Swaminathan et al. |
| 10,350,824 | B2 | 7/2019 | Ng et al. |
| 10,350,876 | B2 | 7/2019 | Ng et al. |
| 10,562,227 | B2 | 2/2020 | Go et al. |
| 10,596,660 | B2 | 3/2020 | McCarthy et al. |
| 10,875,244 | B2 | 12/2020 | Montgomery |
| 2013/0327917 | A1 | 12/2013 | Steiner et al. |
| 2014/0134335 | A1 | 5/2014 | Pridoehl et al. |
| 2015/0028523 | A1 | 1/2015 | Jaker et al. |
| 2016/0339633 | A1 | 11/2016 | Stolyarov et al. |
| 2017/0120334 | A1* | 5/2017 | DeMuth .............. G02B 7/1827 |
| 2017/0128601 | A1 | 5/2017 | DeCiccio et al. |
| 2017/0165908 | A1 | 6/2017 | Pattinson et al. |
| 2017/0173877 | A1 | 6/2017 | Myerberg et al. |
| 2018/0085826 | A1* | 3/2018 | Luo ....................... B23K 26/14 |
| 2018/0200955 | A1 | 7/2018 | Walter et al. |

OTHER PUBLICATIONS

3D Printed Peek Bone Foam; Artstor; University of Pennsylvania Fisher Fine Arts Library Material Collection; https://library.artstor.org/#/public/27529254; Retrieved May 4, 2021.

Cervical interbody fusion cage; CeSPACE® 3D—Aesculap®—anterior / 3D-printed; pp. 1-5; https://www.medicalexpo.com/prod/aesculap/product-70641-957836.html; Retrieved Mar. 22, 2021.

PEEK for medical applications; VESTAKEEP®; Evonik Industries AG; pp. 1-4; Sep. 2013; https://www.modernplastics.com/wp-content/uploads/2015/09/Evonik-VESTAKEEP-PEEK-medical-Flyer-MODERN-Plastics-WEB-4pages.pdf.

FossiLabs Offers 3D Printed 'Fully' Porous PEEK Bone-Like Scaffolding Structures; FossiLabs, LLC; p. 1; Jan. 1, 2020; https://fossilabs.com/pub/FossiLabs_PR_01012020.pdf.

Top 10 3D Printing Solution Providers—2020; Manufacturing Technology Insights; ISSN 2644-2493; pp. 1-2; Mar. 6, 2020; https://3d-printing.manufacturingtechnologyinsights.com/vendors/top-3d-printing-solution-companies-2020.html.

Biomaterials for Implant Applications; VESTAKEEP® PEEK; Evonik Industries; pp. 1-16; Jan. 14, 2020.

Bone Foam, Bone Mesh, Wedge Images; FossiLabs; previously accessible on https://www.fossilabs.com; 2019-2020.

Bone Foam Images; FossiLabs; previously accessible on https://www.fossilabs.com; 2019-2020.

Additive Manufacturing Biomaterials for Permanent Implants, AAOS Annual Meeting, Evonik Promotional Material; VESTAKEEP®; Mar. 13-15, 2019.

Screenshots from FossiLabs Website; previously accessible on https://www.fossilabs.com; 2019-2020.

The Word's first implant grade PEEK Filament for Additive Manufacturing, Vestakeep 3DF Peek Filament, Corporate Presentation, 2019.

* cited by examiner

SYSTEM AND METHOD OF MANUFACTURING A MEDICAL IMPLANT

BACKGROUND

1. Field

Embodiments of the invention relate to a method, system and printing device for printing a customized object, such as a medical implant. More specifically, embodiments of the invention relate to a method, system, and printing device for forming a surgical implant of a polymeric material.

2. Related Art

What is needed is a process for manufacturing a medical implant of a polymeric material that allows for customizing at least the size, shape, and porosity thereof.

The invention describes an improved method and system for manufacturing a surgical device, such as a spinal implant or other medical implant.

The invention describes a printing device for three-dimensional printing that can be programmed to create a custom medical device. The printing device is configured to allow the printing material to be a polymeric material, such as polyaryletherketone (PAEK), or more specifically polyether ether ketone (PEEK).

Prior printing devices were not capable of adequately maintaining the printing material at an optimized temperature during the entire printing process to ensure that each layer of the final printed device was integrally attached to each other layer.

In one embodiment, the final printed object may be a medical implant, such as a spinal implant. The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves and between the interspinous processes that protrude from the vertebrae in the lower back.

Prior medical implants have limited porosity for encouraging bone growth. Known implants may have only surface porosity on an outer surface thereof or discrete openings in defined layers. The present invention provides an improvement over prior implant devices by creating an implant that is porous throughout the entire internal structure. The implant may have a lattice-type structure that allows for interconnected pores extending throughout the entire device. This will advantageously improve the integration of the implant into the body and encourage bone growth therein.

SUMMARY

Embodiments of the invention solve the above-mentioned problems by providing a system and method for printing a customized object, such as a surgical implant, using a printing device having multiple heated elements that are configured to maintain the printing material at a predetermined temperature during the entire printing process.

The construction of the implant according to an embodiment of the invention also allows for customizing the implant to have multiple different portions with different porosities.

A first embodiment of the invention is directed to a printing device for forming a surgical implant from a first material comprising: a housing forming an enclosed space; a print head comprising a heated nozzle for extruding the first material; a planar heated build plate having a top surface for receiving the first material thereon; a reflective plate comprising an active heating element. The reflective plate is located adjacent the heated nozzle and has a bottom surface configured to reflect heat towards the build plate. The reflective plate, the heated build plate, and the heated nozzle are all configured to maintain the first material at a predetermined temperature while forming the surgical implant.

Another embodiment of the invention is directed to a method for using a printing device to create a medical implant, the method comprising: providing a first material for printing the medical implant; providing a printing device; moving the print head and the reflective plate vertically in a Z-plane; and moving the build plate horizontally in a X-plane and in a Y-plane. The printing device comprises: a housing forming an enclosed space; a print head comprising a heated nozzle for extruding the first material; a planar heated build plate having a top surface for receiving the first material thereon; and a reflective plate comprising an active heating element. The reflective plate is located adjacent the heated nozzle and has a bottom surface configured to reflect heat towards the build plate. The reflective plate, the build plate, and the nozzle are all configured to maintain the first material at a predetermined temperature while forming the medical device.

Another embodiment of the invention is directed to a system for 3-D printing a medical device comprising: a printing material for forming the medical device; and a printing device. The printing device comprises: a housing forming an enclosed space; a print head comprising a heated nozzle for extruding the printing material; a planar heated build plate having a top surface for receiving the printing material thereon; a reflective plate comprising an active heating element. The reflective plate is located adjacent the heated nozzle and has a bottom surface configured to reflect heat towards the build plate. The reflective plate, the build plate, and the nozzle are all configured to maintain the printing material at a predetermined temperature while forming the medical device.

Yet other embodiments of the invention are directed to one or more non-transitory computer-readable media storing computer executable instructions, that, when executed by a processor, perform a method of three-dimensionally printing a medical implant, the method comprising: selecting a custom final shape of the implant based at least in part on an anatomy of a particular patient; selecting a first porosity for a first region and selecting a second porosity for a second region of the implant; providing a printing material to a nozzle of a printing device; heating the printing material to at least a glass transition temperature; and dispensing a plurality of layers of the printing material through the nozzle onto the build plate to form the implant.

Another embodiment of the invention is directed to a method for printing a medical implant comprising: providing a printing material and a printing device including a nozzle; selecting a final shape, size, and configuration of the implant; selecting a first porosity for a first region of the implant; selecting a second porosity for a second region of the implant; controlling a dispense rate of the printing material from the nozzle onto a build plate; monitoring a temperature of at least one portion of the printing device by at least one temperature sensor; and adjusting the temperature of at least one element of the printer device to maintain the implant at a predetermined temperature during the entire printing process.

Another embodiment of the invention is directed to a method for forming a porous surgical device by contiguous deposition comprising: providing a printing material; extruding the printing material through a nozzle head; moving the nozzle head vertically in a Z-plane; receiving the printing material on a top surface of a build plate; moving the build plate horizontally in a X-plane and in a Y-plane; and depositing a plurality of layers of the printing material on the build plate to form the surgical device. Depositing the plurality of layers of the printing material further comprises: a) depositing a first layer on the build plate; b) rotating the substantially contiguous pattern by about 36°; and c) depositing a second layer on top of the first layer; and repeating steps a, b, and c until a predetermined number of layers are formed.

A further embodiment of the invention is directed to a selectively porous customizable medical implant made by the process of fused filament fabrication (FFF) by a printer comprising: at least a first region having a first porosity; at least a second region having a second porosity, wherein the pores of the first region are larger than the pores of the second region. The first region may have a lattice structure with interconnected pores. The implant may be made of a polymer, such as polyether ether ketone (PEEK). The implant may further include a coating of hydroxyapatite that extends into the pores.

Another embodiment of the invention is directed to a spinal implant formed by a polymer monofilament printing process, comprising: a top surface, a bottom surface, a peripheral outer surface, and a central opening; and a porous section having a plurality of interconnected pores. The porous section has a first plurality of openings on the top surface and a second plurality of openings on the bottom surface. The implant shape and pore size is selectable for customizing the implant to a particular patient.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1A:
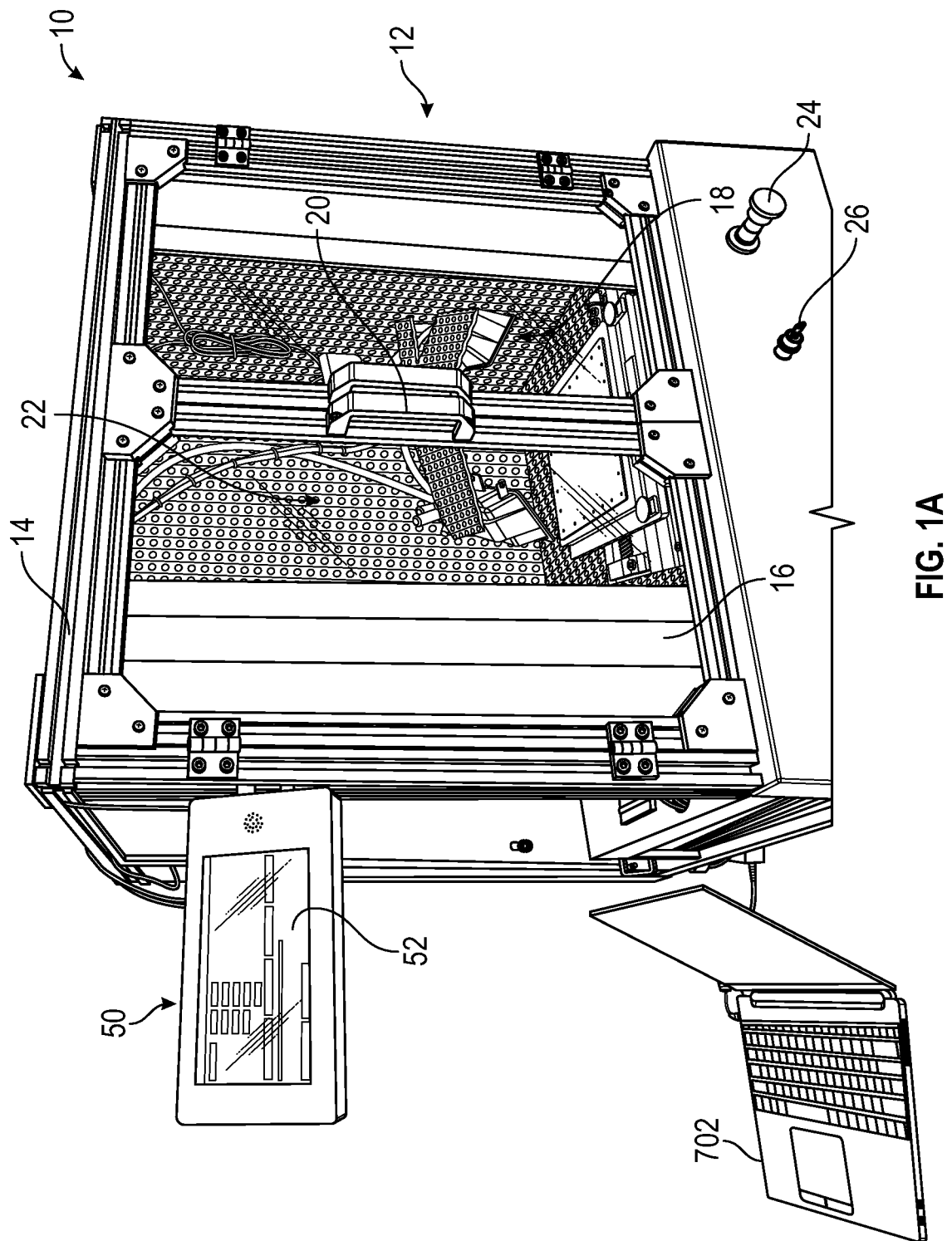
FIG. 1A is a perspective view of the exterior of a first embodiment of the printing device of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Figure 1B:
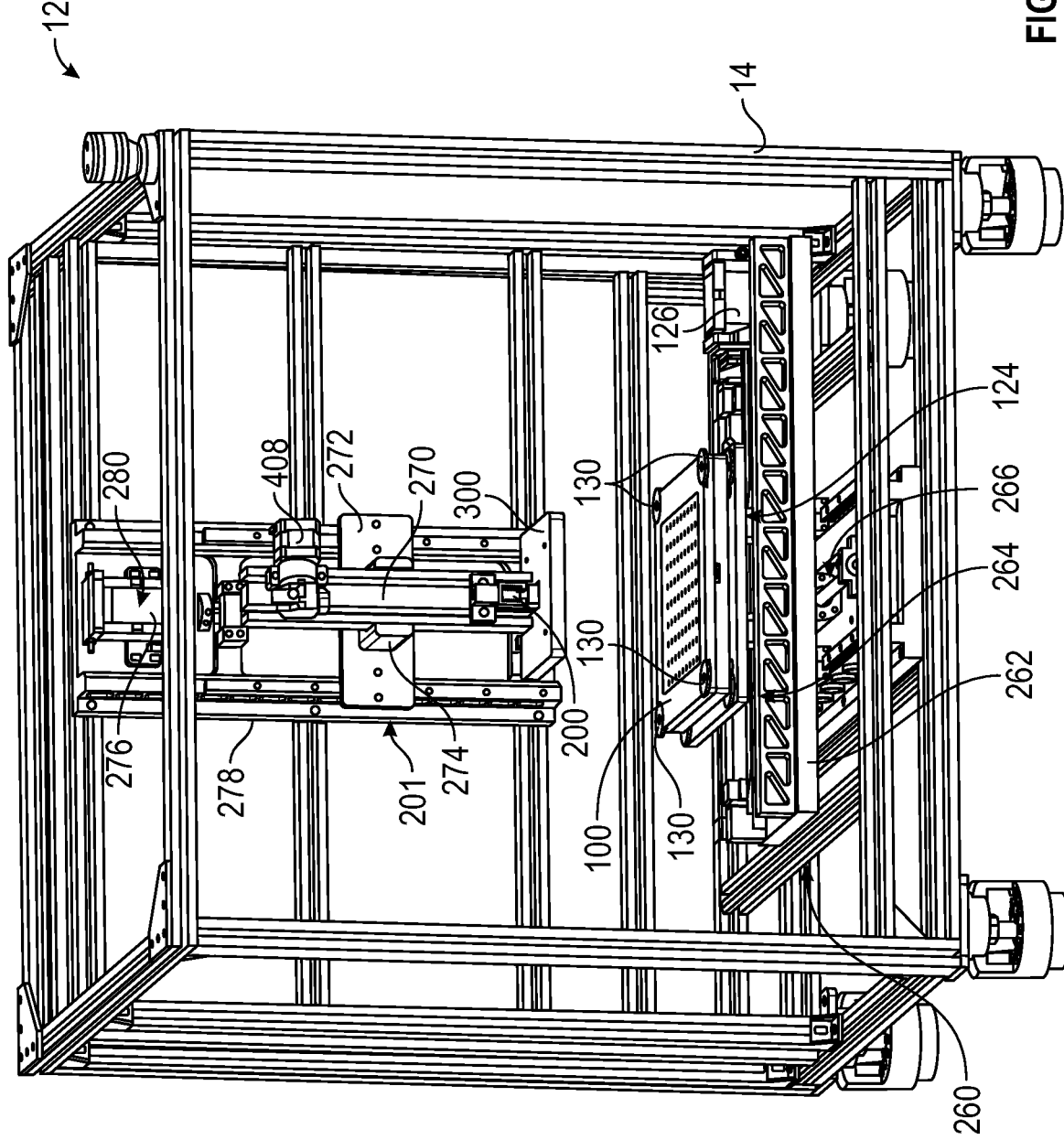
FIG. 1B is a schematic view of the interior of the first embodiment of the printing device.

FIGS. 1A-1B illustrate one embodiment of printing device 10. Printing device 10 may be a three-dimensional printer or an additive manufacturing printer, which is configured to form printed objects 800 from a printing material. In some embodiments, printing device 10 may be used to manufacture objects 800 using any known or yet to be discovered method of additive manufacturing, including but not limited to inkjet, material extrusion, light polymerized, powder bed, laminated, powder fed, or wire methods of additive manufacturing. In some embodiments, printing device 10 is a fused filament fabrication (FFF) printer. In some embodiments, printing device 10 is supplied with a printing material, such as PAEK, PEEK, polyetherketoneketone (PEKK), and/or other high-performance plastics, and combinations thereof. Additional printing materials include acrylonitrile butadiene styrene (ABS), polylactic acid (PLA), poly-ethylene terephthalate (PET), poly-ethylene trimethylene terephthalate (PETT), nylon filament, polyvinyl alcohol (PVA), sandstone filament, and combinations thereof. Printing material may be supplied to the printing device 10 in multiple forms. In one embodiment, printing material is supplied in a filament form.

FIG. 1A shows the exterior of printing device 10 comprising a housing unit 12. Housing unit 12 may comprise a frame 14 for supporting and enclosing the components of printing device 10. In some embodiments, frame 14 may be generally be designed as a rectangular housing unit, however, it will be appreciated that frame 14 may be designed in any geometric shape or design, such as cylindrical or square. Furthermore, the dimensions of frame 14 may likewise vary depending on the embodiment, and for example, may be configured based on the dimensions of the final printed object. For example, in some embodiments, frame 14 may comprise the following dimensions: a length of about 25 inches to about 45 inches; a width of about 18 inches to 38 inches; and a height of about 33 inches to 53 inches. Frame 14 may be constructed from any suitable material, including but not limited to metallic alloys such as aluminum, magnesium, titanium, stainless steel, or other known structural frame materials.

Figure 5:
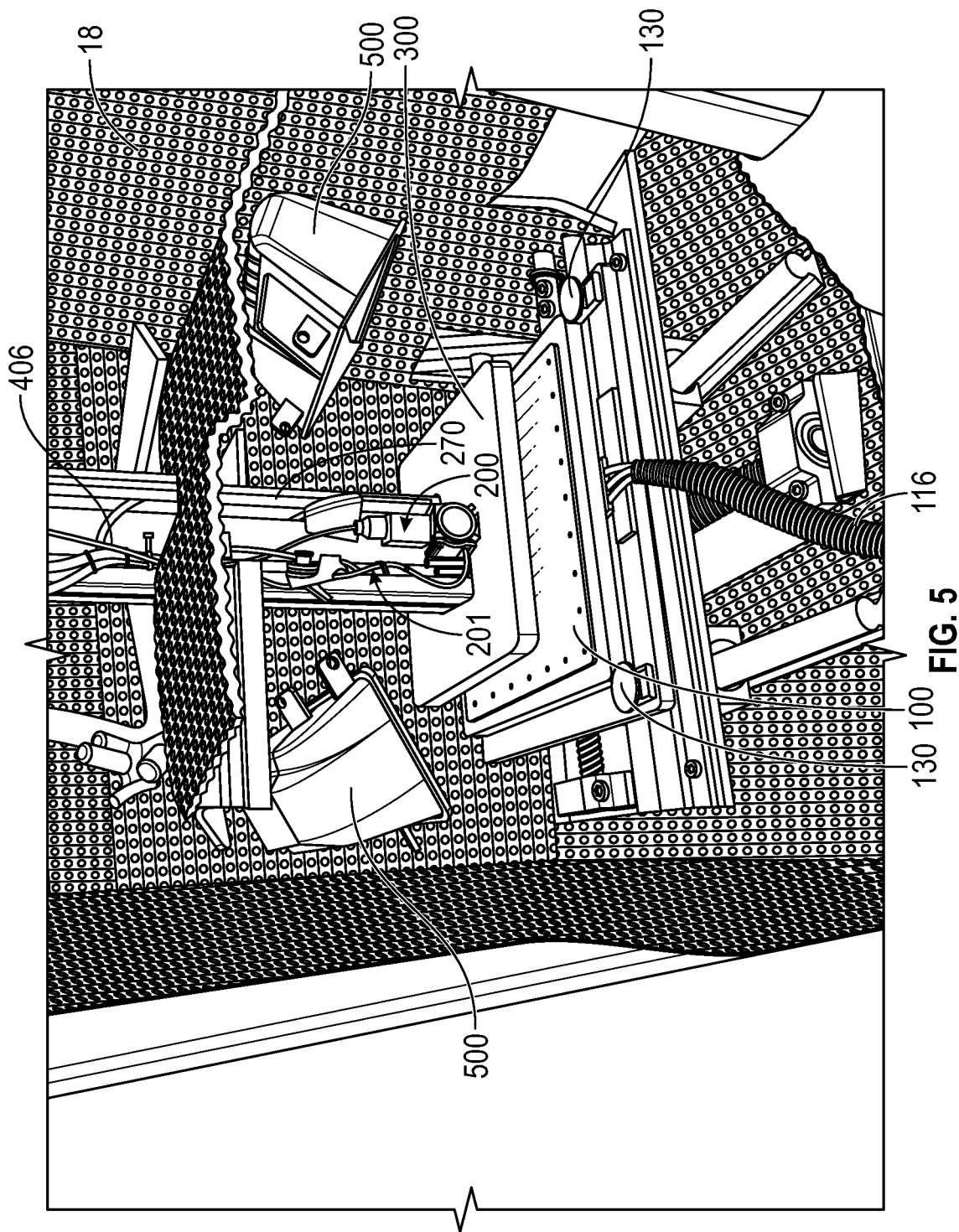
FIG. 5 is a perspective view of the interior of the printing unit of the invention.

In some embodiments, frame 14 may support at least one panel 16 thereon. In some embodiments, multiple panels 16 may be provided to form an enclosure for protecting printing object 800. For example, panels 16 may form a cube-like enclosure, as seen in FIG. 5. Panels 16 may provide a partially or fully closed-frame design to aid in maintaining a desired temperature inside housing unit 12. The partially or fully closed-frame design may also prevent a user from contacting the inside of the printing device 10 during operation.

Panels 16 may be constructed from any suitable material, including but not limited to metallic alloys, such as aluminum, magnesium, titanium, stainless steel, or other known materials. In some embodiments, panels 16 may be composed of at least one material having a thermally insulating property to aid in maintaining the desired temperature inside housing unit 12 during operation. In some embodiments, at least one interior surface of panel 16 may include a thermally insulating material 18. In some embodiments, thermally insulating material 18 may be applied as a lining or additional layer, may be manufactured into panels 16, or may be applied as a coating on a surface of panels 16. In some embodiments, panels 16 may be manufactured from a material that has inherent thermally insulating properties or such material may be added during the manufacturing process.

In some embodiments, frame 14 may further comprise at least one means for accessing the interior of housing unit 12, such as one or more doors 20 or a hatch. In some embodiments, doors 20 are configured with handles and rotate on hinges. In some embodiments, one or both doors 20 may further comprise a viewing portal 22 or window for observing the interior of housing unit 12 during operation of printing device 10. Viewing portal 22 may be constructed from any suitable transparent or translucent material and, for example, may be laminated safety glass. In some embodiments, viewing portal 22 may be located on one of panels 16 supported on frame 14. In some embodiments, there may be a plurality of viewing portals 22 located on door 20, panels 16, or any combination thereof. Printing device 10 may also have a safety shut-off switch 24, which may be located on a front panel. Printing device 10 may also have a key lock 26 for locking the doors 20 while the printing device 10 is in operation. In some embodiments, the printing device 10 automatically locks the door 20 to prevent a user from opening the chamber during printing.

As further illustrated in FIG. 1A, printing device 10 may comprise a control system 50, which is communicatively coupled to printing device 10. Control system 50 may comprise a processor, which as described in greater detail herein, may be configured to receive custom design parameters from a user for controlling printing device 10 before and/or during operation. Control system 50 may further comprise a display 52. Display 52 may provide an interface for inputting instructions, such as a touch-screen interface. Display 52 may also provide any information to a user about printing device 10 before, during, and after operation. For example, display may provide information that may be required for pre-operation, post-operation, diagnostic testing, and/or troubleshooting. An additional computer 702 may be connected to printing device 10. Computer 702 may allow a user to input additional instructions and is configured to interact with control system 50.

FIG. 1B illustrates a schematic view of the interior of housing unit 12, illustrating additional components of printing device 10. It is noted that panels 16 are not shown in this view in order to better see the other internal components. In some embodiments, printing device 10 may comprise a build plate 100, a print head 200, and a reflector unit 300. As can be seen in FIG. 1B, frame 14 supports an upper assembly 201 and a lower assembly 260. Lower assembly 260 includes a support structure 262 for receiving build plate 100 thereon. Upper assembly 201 includes a support structure 278 for receiving print head 200 and reflector unit 300 thereon. In some embodiments, build plate 100 may be positioned below print head 200 and reflector unit 300. Build plate 100 is configured to receive the printed material 400 thereon to form the object 800.

Figure 2A:
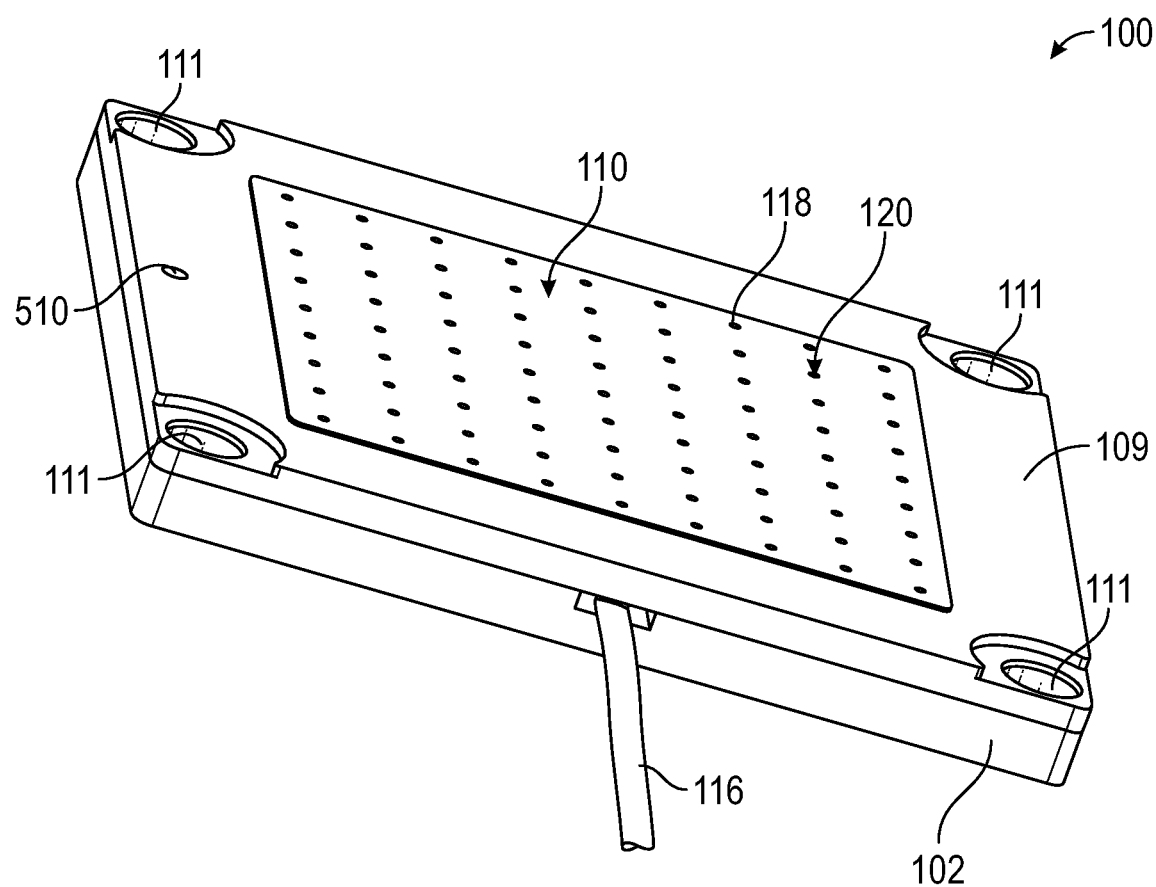
FIG. 2A is a perspective view of a first embodiment of the build plate in an assembled state.
Figure 2B:
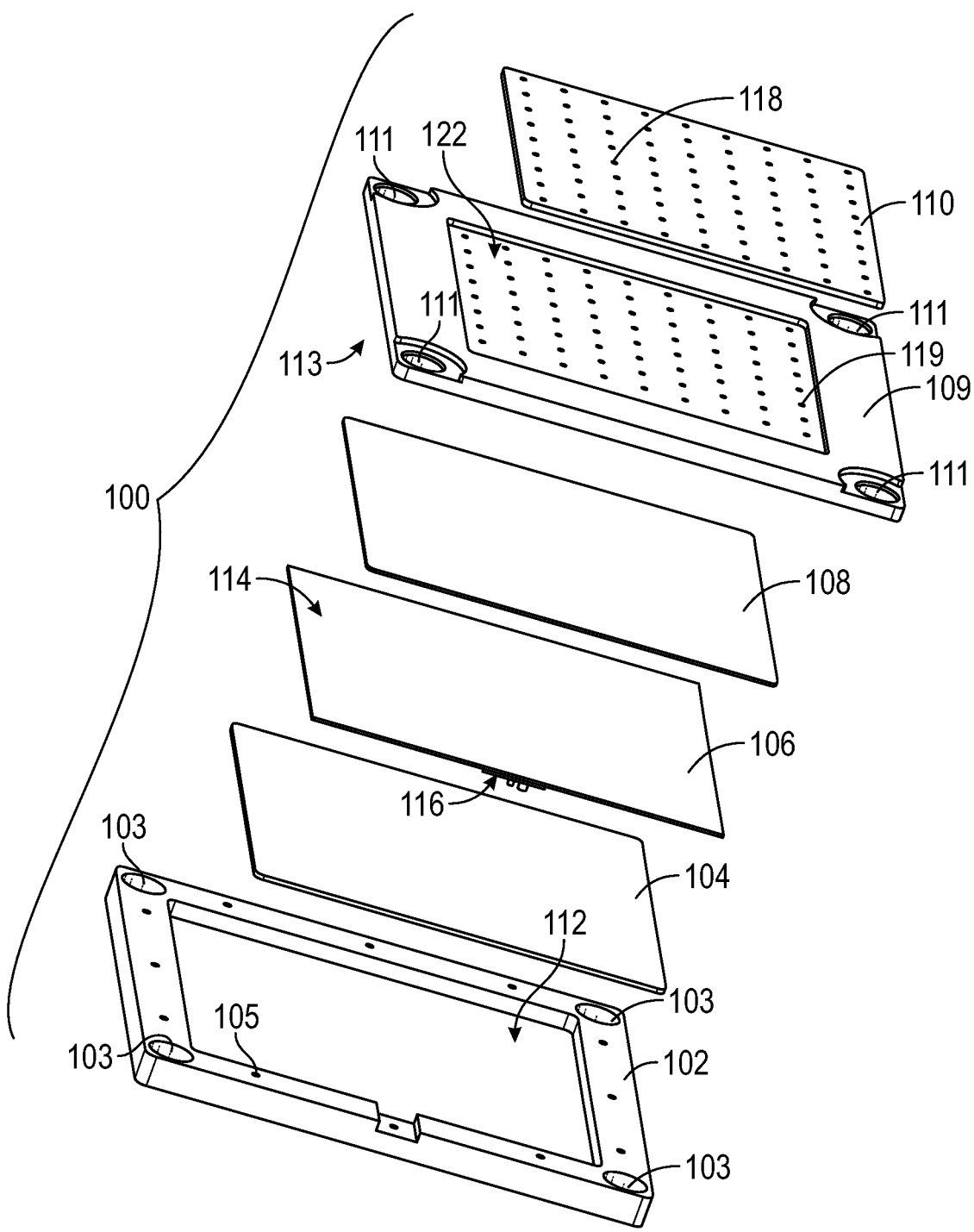
FIG. 2B is an exploded view of the first embodiment of the build plate.

FIGS. 2A-2B illustrate an embodiment of build plate 100. FIG. 2A illustrates a perspective view of build plate 100 in an assembled state and FIG. 2B is an exploded view. In one embodiment, build plate 100 may be designed in a generally rectangular shape and configuration. However, in other embodiments build plate 100 may be designed in any geometric shape and may be for example circular, triangular, rectangular, pentagonal, or any other polygonal geometric shape or design. Furthermore, it will be appreciated that the size and shape of build plate 100 may also vary depending on the embodiment and the desired use. However, build plate 100 may generally be designed such that it is larger than the desired dimensions of the object 800 to be printed. Thus, the entirety of the printed object 800 may be received within the interior perimeter of build plate 100.

With reference to FIG. 2B, in some embodiments, build plate 100 may comprise a plurality of layers. In some embodiments, build plate 100 comprises a flat and planar design. In some embodiments each of the plurality of layers of build plate 100 may comprise a generally flat and planar shape and design. Alternatively, in some embodiments each of the plurality of layers may comprise other shapes and designs, and for example, may comprise curved, concave, or convex designs. In one embodiment, as seen in FIG. 2B, build plate 100 may comprise a bottom frame layer 102, at least one insulating layer 104, at least one heating layer 106, at least one intermediate layer 108, a top frame layer 109 and a top build layer 110. It will be appreciated that in some embodiments, build plate 100 may comprise greater or fewer layers.

In one embodiment, bottom frame layer 102 may be constructed from aluminum. In alternative embodiments, bottom frame layer 102 may be constructed from other materials, such as stainless steel, titanium, or other suitable materials and combinations thereof. In some embodiments, upper surface of bottom frame layer 102 may comprise a recess 112 or formed indention, configured such that at least one other layer of build plate 100 may be placed on and rest in recess 112. Bottom frame layer 102 may include one or more openings 105 for receiving fasteners therein for anchoring the layers of the build plate together. Specifically, the openings 105 may receive fasteners for connecting bottom frame layer 102 to corresponding openings 113 located on the underside of top frame layer 109. Alternatively, bottom frame layer 102 and top frame layer 109 may be connected together by any known means, such as mechanical fasteners or adhesives. Bottom frame layer 102 may further include one or more openings 103 for receiving connectors 130 therein for connecting the build plate 100 to lower assembly 260, as discussed further below.

In some embodiments, build plate 100 may comprise one or more insulating layers 104. Insulating layer 104 can act as a heat break in build plate 100, limiting, reducing, or eliminating the migration of heat generated by build plate 100 to undesirable locations. In one embodiment, build plate 100 includes insulating layer 104 positioned above and adjacent to bottom frame layer 102. In one embodiment, insulating layer 104 may be planar and generally be configured in the same shape as recess 112 such that it is received entirely within recess 112. In one embodiment, insulating layer 104 has a thickness of about 0.2 inches to about 0.3 inches. In some embodiments, insulating layer 104 may have a thickness in a range of from about 0.1 inch to about 0.75 inches. It will be appreciated that in some embodiments, insulating layer 104 can be constructed from a single material, alloy, or polymer. In alternative embodiments, insulating layer 104 can be constructed from a mixture of multiple materials, alloys, or polymers. Insulating layer 104 can be constructed from a variety of different materials, alloys, or polymers, each having different thermally insulating properties. For example, in one embodiment, insulating layer 104 can be at least partially constructed from mica. In one embodiment, insulating layer 104 can be at least partially constructed from ceramic. In one embodiment, insulating layer 104 can be at least partially constructed from PEEK, PAEK, or PEKK.

Alternatively, in some embodiments, insulating layer 104 can comprise a plurality of distinct units positioned in recess 112 in a spaced manner. The plurality of units may be designed as any geometric shape and may be for example, round, triangular, rectangular, pentagonal, or any other polygonal shape. In some embodiments, the plurality of units are round and circular in shape. The plurality of units may have any desired thickness, such as about 0.25 inch. Alternatively, in some embodiments the thickness of the plurality of units may be 0.1-0.75 inches thick. The number of units may vary, depending on the embodiment, and may consist of any number of desired units. In some embodiments, insulating layer 104 may comprise five thermally insulating units.

In some embodiments, build plate 100 may further comprise at least one heating layer 106. In one embodiment, heating layer 106 may be positioned above and adjacent to insulating layer 104 and, in some embodiments, may rest against the top surface of insulating layer 104. Heating layer 106 can comprise a selectively operable and/or programmable heating element 114 for generating heat and for maintaining a predetermined temperature of the top build layer 110 of build plate 100 during operation. In some embodiments, heating layer 106 can be a solid layer of material such as silicone, aluminum, titanium, platinum, or other metal alloys with conductive properties that is capable of generating heat. In some embodiments, heating layer 106 can be coupled to wiring, cables, coils, or other conductive circuitry 116 capable of transferring an electric current to the heating layer 106. Conductive circuitry 116 can transfer electricity from an external source, such as a battery or standard electrical outlet, to heating layer 106 for generating heat. In some embodiments, heating element 114 and/or conductive circuitry 116 can be communicatively coupled to control system 50. Control system 50 can be programmed and/or configured to receive instructions from a user to increase and/or decrease the heat generated by heating element 114 as desired during operation.

In some embodiments, build plate 100 may further comprise at least one intermediate layer 108. In some embodiments, intermediate layer 108 can be positioned above and adjacent to heating layer 106. In some embodiments, intermediate layer 108 can be placed above and rest on the top surface of heating layer 106. Intermediate layer 108 can be designed in any geometric design or shape, such as circular, triangular, rectangular, pentagonal, or any other polygonal shape. In some embodiments, intermediate layer 108 may generally comprise the same shape as build plate 100. The dimensions of intermediate layer 108 can further vary depending on the embodiment. In some embodiments, intermediate layer 108 will have dimensions such that it can be placed within recess 112, along with insulating layer 104 and heating layer 106.

In some embodiments, intermediate layer 108 can act as a diffuser, distributing the heat generated by heating layer 106 in a uniform and even manner. In some embodiments, intermediate layer 108 can aid in preventing, reducing, or eliminating any focused pockets of heat, or hot spots. Intermediate layer 108 acts to dissipate the hot spots across the entirety of its surface. The dissipation of hot spots can aid in forming a uniform distribution of heat, which creates a more optimum environment on top surface of build plate 100 for printing an object 800. In one embodiment, intermediate layer 108 is constructed from stainless steel, however, it will be appreciated that intermediate layer 108 can be constructed from any suitable material having heat dissipation properties.

In some embodiments, build plate 100 may further comprise a top frame layer 109. Top frame layer 109 is positioned directly above and adjacent to intermediate layer 108. Top frame layer 109 may be constructed from aluminum, titanium, stainless steel, or any other suitable material, or combinations thereof. In some embodiments, top frame layer 109 cooperates with bottom frame layer 102 to enclose insulating layer 104, heating layer 106, and intermediate layer 108 therebetween. Top frame layer 109 and bottom frame layer 102 may have similar dimensions such that they fit together. Top frame layer 109 may further include one or more openings 111, which may align with one or more openings 103 in bottom frame layer 102 for receiving connectors 130 therein. In some embodiments, openings 111 and openings 103 are located at the four corners of top frame layer 109 and bottom frame layer 102, respectively. Connectors 130 may anchor the build plate 100 to the lower assembly 260, as discussed further below. Alternatively or additionally, connectors 130 and openings 111 may further be used for fine bed leveling top build layer 109.

In some embodiments, an upper surface of top frame layer 109 may comprise a recess 122 for receiving a top build layer 110 therein. Thus, top frame layer 109 may have a larger length and width than top build layer 110. In some embodiments, top build layer 110 may have a thickness greater than the depth of recess 122, such that an upper surface of top build layer 110 protrudes therefrom. In some embodiments, top build layer 110 and top frame layer 109 has upper surfaces that are flush with one another to form the upper surface of the build plate 100. In some embodiments, recess 122 includes a plurality of holes 119 for receiving fasteners 120 therein.

In some embodiments, top build layer 110 provides a surface for receiving the printed material thereon to form printed object 800. Top build layer 110 may be designed as any geometric shape or design, including but not limited to circular, triangular, rectangular, pentagonal, or any other polygonal shape. As shown in FIG. 2B, top build layer 110 may be substantially rectangular. For example, in some embodiments, top build layer 110 can comprise a length of about 1.5 inches to about 4.5 inches and further comprise a width of about 1.5 inches to about 4.5 inches. In some embodiments, top build layer 110 includes a plurality of holes 118 that cooperate with holes 119 in top frame layer 109 for receiving fasteners 120 therein. In one embodiment, fasteners 120 may be used to secure top build layer 110 to top frame layer 109. Securing top build layer 110 to top frame layer 109 aids in preventing the top build layer 110 from warping or curving during use. Maintaining a planar structure of the top build layer 110 during operation ensures reliability in the printed object 800 having a flat base. In alternative embodiments, top build layer 110 may be secured to top frame layer 109 through any known fastening method, including but not limited to adhesives or other mechanical fasteners such as for example nails, bolts, or clamps.

In some embodiments, top build layer 110 can also act as a diffuser, distributing the heat generated by heating layer 106 in a uniform and even manner. In some embodiments, top build layer 110 can aid in preventing, reducing, or eliminating any focused pockets of heat, or hot spots. Top build layer 110 acts to dissipate the hot spots across the entirety of its surface. The dissipation of hot spots can aid in forming a uniform distribution of heat, which creates a more optimum environment on top surface of build plate 100 for printing an object 800. In one embodiment, top build layer 110 is constructed from stainless steel, however, it will be appreciated that top build layer 110 can be constructed from any suitable material having heat dissipation properties.

In some embodiments, top build layer 110 may be constructed at least partially from polyetherimide (PEI), PEEK, PAEK, PEKK, UItem™, or other thermoplastic polymers or any combination thereof. In some embodiments, top build layer 110 may be partially or fully constructed of glass, aluminum, stainless steel, or other metallic alloys, or combinations thereof. In some embodiments, top build layer 110 may have a thickness of about 0.25 inches. In some embodiments, the thickness of top build layer 110 may be from about 0.1 inch to about 0.75 inch.

As discussed above, in some embodiments top build layer 110 may comprise a plurality of holes 118 or void spaces in the top surface thereof. The number and placement of holes 118 may vary, depending on the embodiment. In some embodiments, the number and placement of holes 118 may correspond to the number and placement of holes 119 in top frame layer 109. Holes 118 may be machined or manufactured into top build layer 110 during construction, or alternatively, may be placed in top build layer 110 after construction. In some embodiments, holes 118 may be selectively positioned in rows and/or columns of a predetermined quantity. In some embodiments, holes 118 may be placed randomly, without a predetermined selection of placement. In some embodiments, holes 118 may be througholes extending completely through top build layer 110, thereby creating continuous openings into top build layer 110. Alternatively, in some embodiments one or more holes 118 may be defined partially into top build layer 110 and stop short of creating a continuous opening entirely through top build layer 110. In some embodiments, top build layer 110 may comprise a combination of througholes 118 and partial holes 118.

In some embodiments, as heat generated by heating layer 106 begins to move up in the z-plane of the build plate 100 and reaches top build layer 110, holes 118 may aid in distributing the heat across the entire surface of top build layer 110. In some embodiments, holes 118 may also aid in dissipating the heat as it reaches top build layer 110. As described in greater detail below, printing device 10 may further comprise additional heat sources, and in some embodiments the additional heat sources may be located axially above top build layer. In addition to distributing and dissipating heat directed from the lower heating layer 106, top build layer 110 may further distribute and dissipate heat from the above additional heat sources, in a similar manner. The distribution or dissipation of heat can help to prevent, reduce, or eliminate the build-up of hot spots or heat sinks on top build layer 110. The reduction or elimination of hot spots and heat sinks can be beneficial during operation, as this may cause warping or distortion of the top build layer 110 and/or of the final printed object 800. In some embodiments, top build layer 110 may be comprised of a thermal expansion material, that expands as the temperature within housing unit 12 increases. In such an embodiment, holes 118 can aid in providing spacing or clearance for the material to expand, thus preventing and/or reducing warping of top build layer 110.

In some embodiments, at least some of the void spaces created by holes 118 may be filled with a compatible element. In some embodiments, one or more holes 118 may receive mechanical fasteners 120 such as screws, nails, glue or epoxy, or other suitable fasteners therein. In some embodiments, fasteners 120 may be constructed from aluminum, titanium, stainless steel, or other metallic alloys. In some embodiments, fasteners 120 may be constructed from a thermoplastic polymer. In some embodiments, fasteners 120 may be constructed from any known or yet to be discovered material that is capable of maintaining its form and shape up to the highest temperature range that printing device 10 is capable of achieving. Fasteners 120 may aid in increasing the heat distribution or dissipation properties of top build layer 110. For example, fasteners 120 may aid in distributing or dissipating heat generated from heating layer 106 across the surface of top build layer 110.

In some embodiments, fasteners 120 may be used to mechanically couple top build layer 110 to at least one of the plurality of layers of build plate 100, such as top frame layer 109. Alternatively, in some embodiments, each of the plurality of layers of build plate 100 may secured together through the use of mechanical fasteners, such as screws, bolts, or epoxy.

For example, as illustrated in FIG. 2B, in some embodiments bottom frame layer 102 may form the bottom of build plate 100. Insulating layer 104 may be positioned within recess 112. Heating layer 106 may then be placed within recess 112 adjacent to and on top of insulating layer 104. Intermediate layer 108 may then be positioned within recess 112 adjacent to and on top of heating layer 106. Top frame layer 109 may then be placed on top of bottom frame layer 102, acting as an enclosure for insulating layer 104, heating layer 106, and intermediate layer 108. Top frame layer 109 and bottom frame layer 102 can then be coupled or secured together using mechanical fasteners, adhesives, or other fastening methods. Top build layer 110 may be positioned within recess 122 of top frame layer 109 and anchored therein, as discussed above.

In some embodiments, build plate 100 may further include at least one optional or additional cooling device (not shown) to aid in regulating the temperature of build plate 100. In some embodiments, a cooling device may be located internally within build plate 100. In some embodiments, printing device 10 may include an additional cooling device located externally from build plate 100. Cooling device may be configured as any known system or device for cooling hardware or parts and may be configured as a fan, a baffle, a water-cooling device, or any other known cooling devices or systems. In some embodiments, there may be a plurality of cooling devices for cooling heated build plate 100.

In some embodiments, build plate 100 can be positioned below print head 200 in the z-plane and provide a printing surface for receiving printing material thereon. In some embodiments, printing material can be printed directly onto top build layer 110. In some embodiments, heat generated by heating layer 106 can transfer up through build plate 100 and reach top build layer 110, where the heat may then be distributed across the top surface of top build layer 110. This distribution of heat can reduce, prevent, or eliminate the presence of heat sinks or hot spots, which can cause warping of printed objects 800 and/or top build layer 110.

In some embodiments, a heated build plate 100 can aid in improving the quality of the printed object 800. For many printing filaments and materials, there can be a tendency for the material to crystallize if it cools too quickly after being dispensed, Therefore, it is advantageous to maintain the temperature of the printing material while it is on the printing surface, such as top build layer 110. In some embodiments, heat generated from heating layer 106 can transfer up through the z-plane until reaching top build layer 110. Once reaching top build layer 110, the heat can dissipate or otherwise be distributed throughout top build layer 110. The heat generated from heating layer 106 and dissipated in top build layer 110 can create a heating effect to the printed object, thereby preventing or reducing crystallization of the printed object 800.

In some embodiments, build plate 100 may be configured to operationally and selectively move in the z-plane. Lower assembly 260 includes a support structure 262 for receiving build plate 100 thereon. In some embodiments, build plate 100 may be secured to support structure 262 via connectors 130, whereby connectors 130 anchor build plate 100 to support structure 262. Alternatively or additionally, in some embodiments build plate 100 may be configured to move in the x-y plane. In some embodiments, as illustrated in FIG. 1B, build plate 100 may be attached via support structure 262 to a motorized lower drive train 124 or mechanized platform having a motor 126, that can be selectively and controllably configured to move in the z-plane and/or the x-y plane. In some embodiments, motorized lower drive train 124 can comprise a first lower sub-assembly 264 and a second lower sub-assembly 266. In some embodiments, first lower sub-assembly 264 can be configured to move build plate 100 in the x-plane. In some embodiments, second lower sub-assembly 266 can be configured to move build plate 100 in the y-plane. Alternatively, in some embodiments, first lower sub-assembly 264 can be configured to move build plate 100 in the y-plane. In some embodiments, second lower sub-assembly 266 can be configured to move build plate 100 in the x-plane. In some embodiments, lower drive train 124 can be communicatively coupled to control system 50. Control system 50 can be programmed and/or configured to command lower drive train 124 to move up and/or down in the z-plane and/or to move laterally in the x-y plane. In some embodiments, control system 50 can respond to manual controls for moving build plate 100. In some embodiments, control system 50 can be programmed with a machine learning algorithm and instructions to move build plate 100 in response to certain predetermined parameters such as, for example, temperature of the interior of housing unit 12, temperature of the printed object 800, and/or distance between build plate 100 and print head 200. In alternative embodiments, lower drive train 124 may be manually operated by a non-motorized means. For example, lower drive train 124 could be manually operated by a mechanical lift. It will be appreciated that there are numerous methods and systems that could be implemented for moving build plate 100 in the z-plane and/or in the x-y plane, and any suitable method or system could be implemented in the present invention.

Figure 3A:
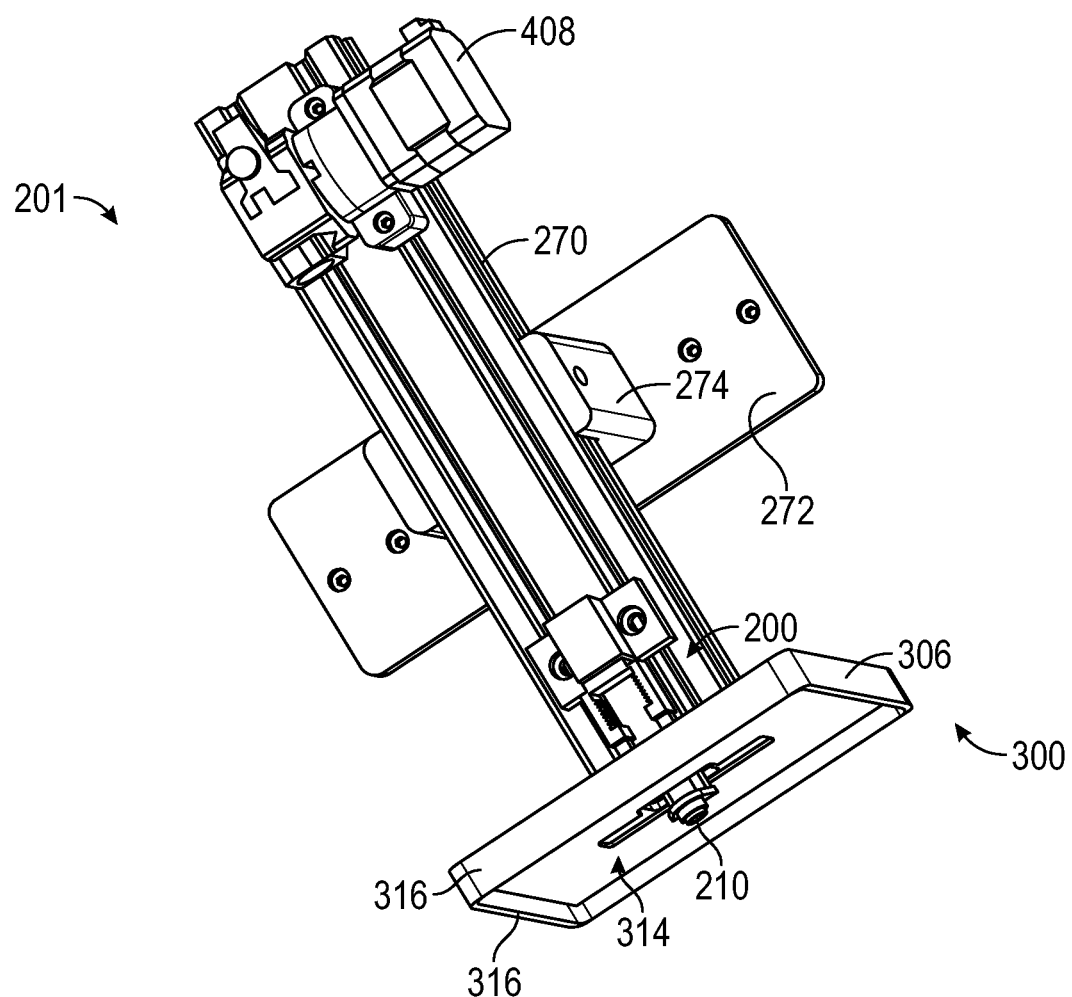
FIG. 3A is a perspective view of a first embodiment of the upper assembly of the invention in an assembled state.
Figure 3B:
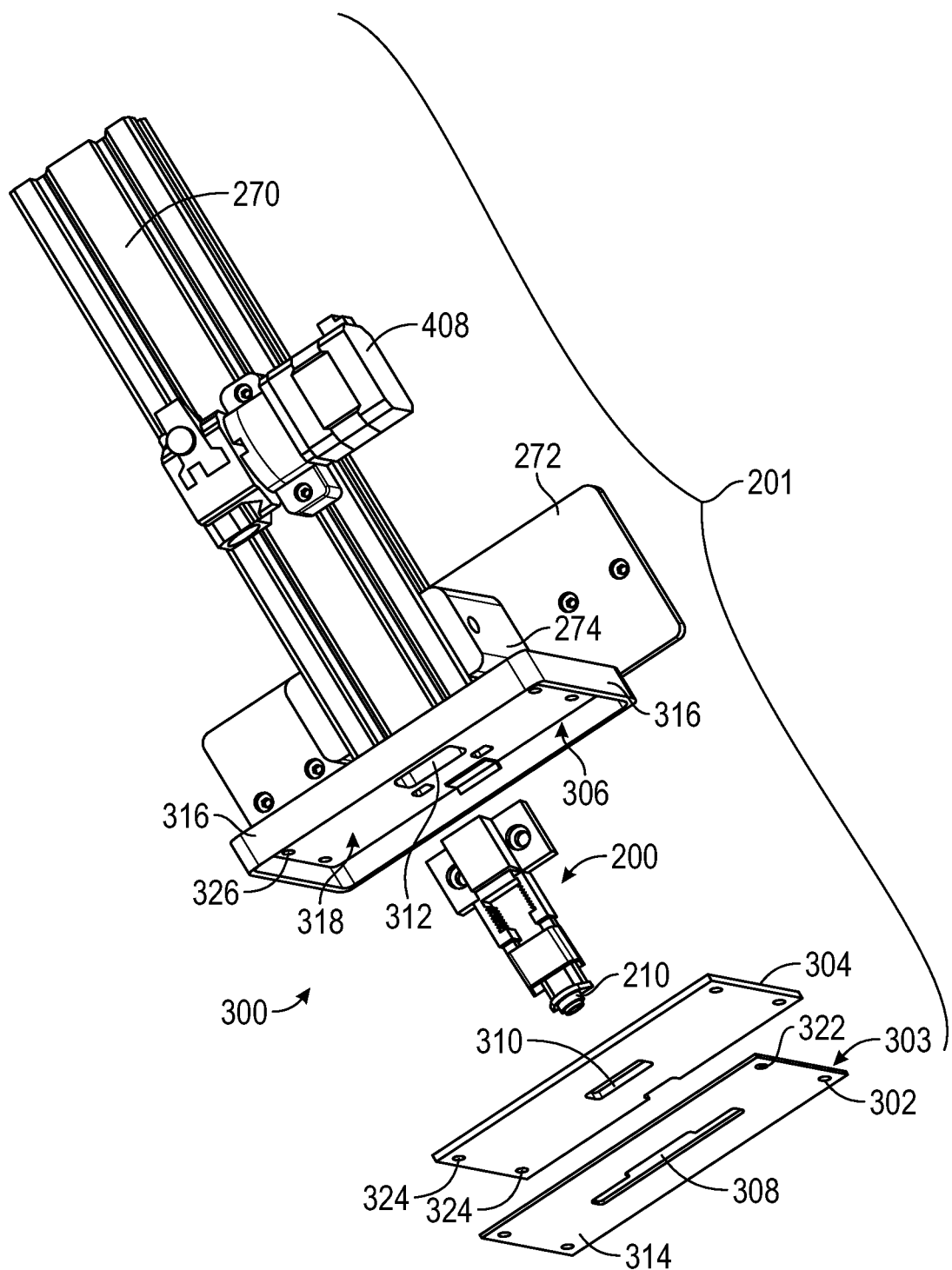
FIG. 3B is an exploded view of the first embodiment of the upper assembly.

FIGS. 3A-3B illustrate an embodiment of a portion of upper assembly 201. FIG. 3A illustrates a perspective view of upper assembly 201 in an assembled state and FIG. 3B shows an exploded view thereof.

In some embodiments, upper assembly 201 may be used for heating and dispensing a printing material, such as printing filament 400. As can be seen in FIG. 1B, upper assembly 201 includes a support structure 278 for receiving print head 200 and reflector unit 300 thereon. Upper assembly 201 includes coupling plate 272, bracket 274, and vertical support 270. Upper assembly 201 also includes a motor 276 operatively connected to an upper drive train 280. In some embodiments, coupling plate 272 is anchored to support structure 278 and bracket 274 is anchored to coupling plate 272. Bracket 274 receives vertical support 270 therein and is anchored thereto. In some embodiments, print head 200 and reflector unit 300 are secured to vertical support 270.

In some embodiments, vertical support 270 may be coupled to an upper drive train 280, for selectively moving vertical support 270 and the components secured to vertical support 270. Upper drive train 280 may be configured to selectively move in the z-plane. In some embodiments, upper drive train 280 can be communicatively coupled to control system 50. Control system 50 can be programmed and/or configured to command upper drive train 280 vertically in the z-plane. In some embodiments, upper drive train 280 may additionally or alternatively be configured to selectively move in the x-y plane. In some embodiments, control system 50 can respond to manual controls for moving print head 200 and reflector unit 300. In some embodiments, control system 50 can be programmed with a machine learning algorithm and instructions to move print head 200 in response to certain predetermined parameters, such as for example the temperature of the interior of housing unit 12, the temperature of the printed object 800, or the distance between build plate 100 and print head 200. In alternative embodiments, upper drive train 280 may be a manually operated by a non-motorized means. For example, upper drive train 280 could be manually operated by a mechanical lift. It will be appreciated that there are numerous methods and systems that could be implemented for moving print head 200 and reflector unit 300 in the z-plane and/or the x-y plane, and any suitable method or system could be implemented in the present invention.

Figure 4:
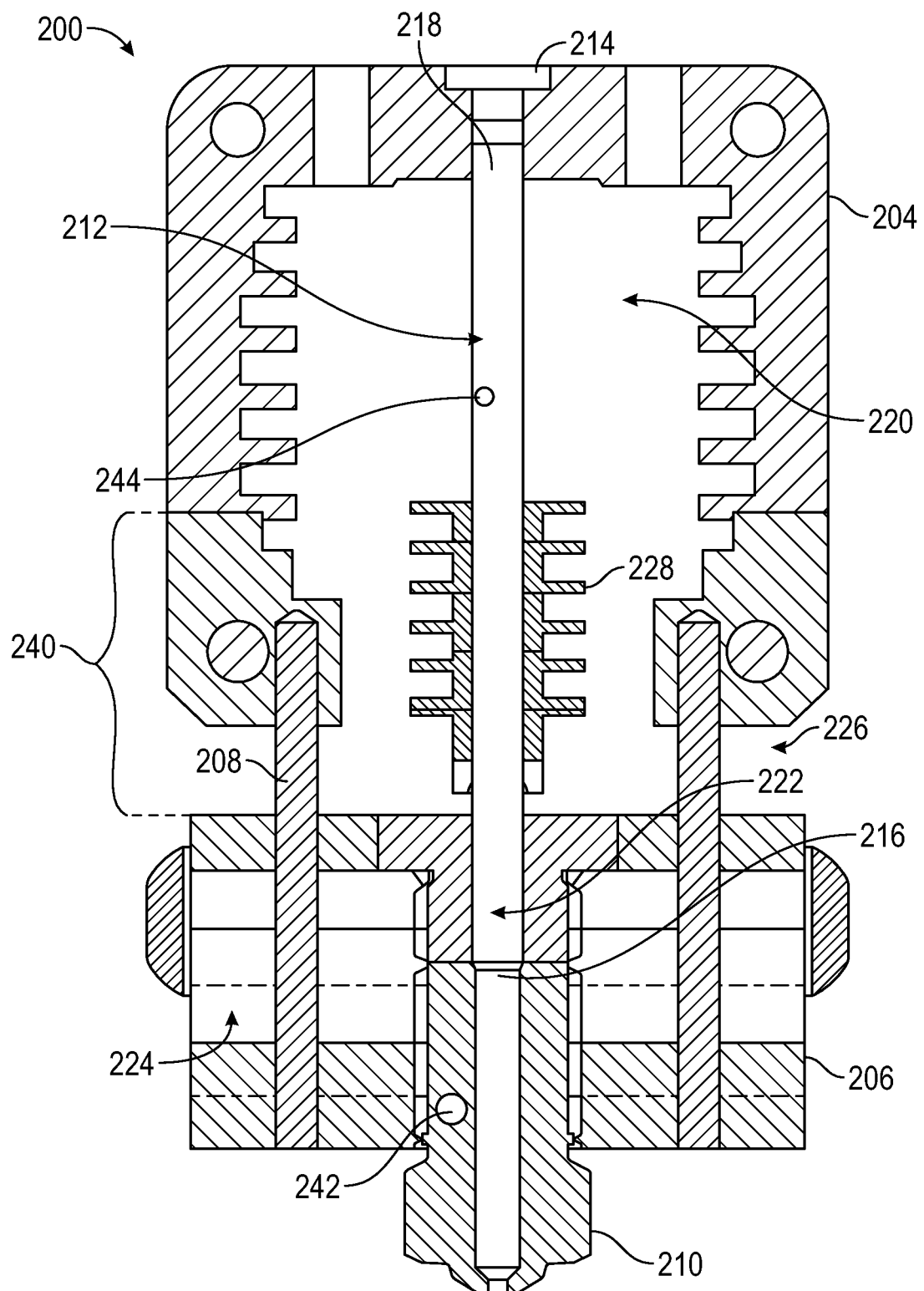
FIG. 4 is a cross-sectional view of an embodiment of the print head of the invention.

FIG. 4 illustrates a cross-sectional view of print head 200. In some embodiments, print head 200 may consist of various components and parts for heating and dispensing printing material, such as printing filament 400. In some embodiments, print head 200 may comprise a cooler 204, a heater 206, at least one bridge 208, and a nozzle 210. Print head 200 may further comprise a feed tube 212 for feeding printing material 400 into and through print head 200 prior to dispensing printing material 400 onto build plate 100. Feed tube 212 may be constructed from a metal, such as aluminum, titanium, or any other suitable material. In some embodiments, feed tube 212 may extend generally axially. Feed tube 212 may comprise an inlet 214 for receiving a forwardly driven printing filament 400 of a solid disposition material. Feed tube 212 may further comprise an outlet 216, positioned downstream from inlet 214. An hollow internal passage 218 may connect inlet 214 to outlet 216. Internal passage 218 may comprise an upstream portion 220 and a downstream portion 222. In some embodiments, feed tube 212 may have an inner surface coated with an adhesion-reducing substance to prevent the printing material 400 from sticking thereto. For example, inner surface of feed tube 212 may be coated with electroless nickel, an electroless nickel-boron composite, tungsten disulfide, molybdenum disulfide, boron nitride, diamond-like carbon, or any other suitable material, or combinations thereof.

In some embodiments, heater 206 may be thermally coupled with downstream portion 222. Heater 206 may be used for heating the printing filament 400 as the printing filament 400 passes through feed tube 212 and reaches downstream portion 222. Heater 206 may comprise a heating element 224, which can be selectively controlled to heat printing filament 400. In some embodiments, heating element 224 may be a thermally conductive material comprising a heater, such as a glow wire or conductive circuitry. In some embodiments, heating element 224 may be any known electrical or chemical heating element. In some embodiments, heater 206 may be communicatively coupled to control system 50, for selectively controlling the parameters of heater 206. For example, control system 50 may control when heater 206 is activated, the duration of the activation, and/or the amount of generated heat such that printing material 400 may be maintained at the desired temperature. In some embodiments, heater 206 may be manually controlled and adjusted by inputs entered into control system 50. In some embodiments, heater 206 may be automatically controlled based on predetermined parameters and adjusted by control system 50 for automatically regulating temperature of printing material 400 during operation.

In some embodiments, heater 206 may be heated to a temperature that is capable of melting printing filament 400 as printing material 400 is transported through downstream portion 222. For example, in some embodiments printing material 400 may be a PEEK filament. Heater 206 may heat printing material 400 to at least 430° C. In some embodiments, heater 206 can be configured to heat printing material 400 from about 130° C. to about 500° C. Printing material 400 may be selected from any known material or filament for printing or additive manufacturing, and heater 206 can be configured to heat the printing material 400 to at least a melting temperature.

In some embodiments, cooler 204 may be thermally coupled with upstream portion 220 and can be used for regulating the temperature of printing filament 400 as it passes through feed tube 212. In some embodiments, cooler 204 may be spaced generally axially upstream from heater 206 with a defined gap 226 or space separating cooler 204 from heater 206. Gap 226 may be filled with at least one bridge 208, providing a rigid mechanical connection between heater 206 and cooler 204. In some embodiments, cooler 204 may comprise a thermoelectric cooler or a heat sink comprising heat-conductive material. In some embodiments, cooler 204 may comprise a strain-hardened stainless steel surgical tubing, which may have a thermal conductivity of less than about 15 W/mK, a tensile strength of greater than about 100 MPA, and a surface roughness of less than about 0.5 µm. In some embodiments, cooler 204 may comprise an internal heat transfer passage (not shown) configured to receive a cooling fluid. In some embodiments, a heat transfer passage may be configured to receive air for cooling. In some embodiments, upstream portion 220 may further be coupled with at least one secondary cooler 228 for directly cooling printing material 400.

In some embodiments, print head 200 may be configured to comprise a hot zone 240. Hot zone 240 may generally be a defined space, void, or heat break zone positioned approximately in the area between heater 206 and cooler 204 and secondary cooler 228. In some embodiments, hot zone 240 can provide a clean line of separation, separating the heat generated from heater 206 from the cooler temperatures defined by the cooler 204 and secondary cooler 228. For example, as printing material 400 passes through feed tube 212, it is advantageous for the printing material 400 to remain in a solid state until reaching the break zone of hot zone 240. As printing material 400 travels down through downstream portion 222 and reaches hot zone 240, printing material 400 can begin to be heated by heater 206. The heat generated by heater 206 begins to heat and melt printing material 400 only after printing material 400 passes through hot zone 240, transitioning printing material 400 from a solid to a molten liquid state. In some embodiments, the heater 206 comprises a copper alloy, which may have a conductivity of greater than about 300 w/mK, and a tensile strength of greater than about 500 MPA, which is especially resistant to creep at high temperatures. The heat flows efficiently inward through the heater 206 to melt the filament quickly. Hot zone 240 maintains printing material 400 in a solid state until reaching downstream portion 222 surrounded by heater 206. The clean line of separation defined by hot zone 240 further prevents heat creep in feed tube 212. For example, in FFF printing systems, it is problematic to heat printing material 400 prior to dispensing. Heating printing material 400 prior to dispensing can cause the printing material to crystalize, which can lead to imperfections in the final printed object. In some embodiments, hot zone 240 can have a dimension of about 0.5 mm to about 1.5 mm, such that there is minimal space between the solid and the melted material.

Print head 200 may further comprise a nozzle 210, which may be attached to heater 206 and coupled to outlet 216 of feed tube 212. Nozzle 210 may be the lowest positioned part of print head 200 and may further be the final part that printing filament 400 passes through prior to dispensing. Nozzle 210 may be smooth bored or threaded, depending on the embodiment. In some embodiments, an inner surface of nozzle 210 may be coated with an adhesion-reducing material. In some embodiment, the adhesion-reducing material may be electroless nickel, an electroless nickel-boron composite, tungsten disulfide, molybdenum disulfide, boron nitride, diamond-like carbon, or any other suitable material, or combination thereof. The diameter of nozzle 210 may vary, depending on the embodiment, and may be designed to generally match of dimensions of printing material 400. In some embodiments the diameter of nozzle 210 may be selected from a range of about 0.2 mm to about 0.5 mm. Furthermore, it will be appreciated that in some embodiments, nozzle 210 may be removable and replaceable. In some embodiments, a plurality of nozzles 210 each having a different diameter or size may be provided whereby a user may select a desired size. For example, in some embodiments printing material 400 may comprise a filament having a diameter of about 1.75 mm, which requires a nozzle 210 having a diameter of about 0.2 mm to about 0.5 mm. A nozzle 210 having a diameter of 3 mm can be selected from a plurality of nozzles 210 and attached to print head 200 for dispensing a particular printing material 400.

In some embodiments, print head 200 may further comprise one or more sensors 242 for measuring the temperature of printing material 400, feed tube 212, heater 206, cooler 204, and/or any other portion of print head 200. Sensors 242 may be located internally at various locations within print head 200 or alternatively, may be externally located. In some embodiments, sensors may be communicatively coupled to control system 50 and the measurement therefrom may be provided to display 52.

In some embodiments, printing device 10 may comprise a reflector unit 300 that cooperates with print head 200. In some embodiments, reflector unit 300 may be located adjacent to and/or partially surrounding print head 200. In some embodiments, reflector unit 300 comprises a reflective plate 302 having a bottom surface 314 configured to reflect heat towards build plate 100 and/or the printed object 800. In some embodiments, reflective plate 302 may be constructed from a material having heat reflecting properties. For example, reflective plate 302 may be constructed from stainless steel, aluminum, titanium, or other materials having heat reflecting properties. In some embodiments, reflective plate 302 is a thick film stainless steel plate.

Reflective plate 302 may generally comprise any geometric shape and depending on the embodiment may be circular, triangular, rectangular, pentagonal, or any other geometric shape. The dimensions of reflective plate 302 may further vary, depending on the embodiment. In some embodiments, reflective plate 302 may have a dimension that is larger than the dimensions of the object 800 being printed. In some embodiments, reflective plate 302 may have a maximum dimension such that when reflector unit 300 is moved in the x-y plane, reflective plate 302 will not come into contact with frame 14, panels 16, or thermally insulating material 18.

For example, in some embodiments, printing device 10 may be used for printing three-dimensional objects 800, such as medical implants. Such implants may have a dimension of about three inches in width and/or length. In some embodiments, reflective plate 302 may have a dimension that is at least larger than the dimension of the three-dimensionally printed object 800. In some embodiments, reflective plate 302 may have a dimension of about 140 mm$^2$. In some embodiments, reflective plate 302 may have larger or smaller dimensions, such as about 25 mm$^2$ to about 300 mm$^2$.

In some embodiments, reflector unit 300 may be configured to be an active heater. In some embodiments, when in an off or non-energized state, reflector unit 300 may be configured to be a passive heat reflector. In some embodiments, bottom surface 314 of reflective plate 302 reflects heat, which may be generated by build plate 100 or other sources of heat, towards top build layer 110 and/or the printed object 800 during operation. In some embodiments, reflector unit 300 can reflect heat generated from heating layer 106 and thus heat the printed object 800 from multiple directions. For example, in some embodiments the printed object 800 can be heated from below by heating layer 106 and from above by reflector unit 300. The reflection of heat by reflector unit 300 can aid in maintaining a desired temperature of the printed object 800, preventing unwanted crystallization or warping. A controlled heat environment aids in forming a more uniform and structurally sound printed object 800.

In some embodiments, reflector unit 300 may further comprise an active heater 303 configured to be selectively controlled. In some embodiments, active heater 303 may be configured to generate heat, which may be directed towards the top surface of build plate 100 and/or the printed object 800. In some embodiments, active heater 303 may be positioned on top surface of reflective plate 302. In some embodiments, active heater 303 can be constructed from a conductive material, such that when an electric current is applied thereto, the conductive material generates heat. In some embodiments, reflective plate 302 can comprise a plate of at least partially composed of a thermally insulating material, having an active heater 303, such as a glow wire, conductive conduit, or other conductive material positioned on a top surface thereof. The active heater 303 may generate heat when an electric current is applied thereto. Active heater 303 can be coupled to an energy source, such as a battery or electrical outlet, for supplying an electrical current to active heater 303. In some embodiments, an energy source may be incorporated into printing device 10. In some embodiments, an energy source may be external to the printing device 10.

In some embodiments, reflector unit 300 may further comprise a reflector housing 306 and an insulator 304. In some embodiments, insulator 304 may be placed on a spacer, providing a gap between reflective plate 302 and insulator 304. Reflective plate 302 and insulator 304 may be attached and secured within reflector housing 306. In some embodiments, reflector housing 306 may be configured to have the same general shape and design as reflective plate 302. In some embodiments, insulator 304 may be configured to have the same general shape and design as reflective plate 302. In some embodiments, insulator 304 can have dimensions such that it may be placed and secured between reflector housing 306 and reflective plate 302. Reflector housing 306 may include side walls 316 forming a recess 318. Insulator 304 and reflective plate 302 may be received within recess 318 of reflector housing 306, as seen in FIGS. 3A and 3B. In order to anchor the reflector unit 300 together, in some embodiments, plate 302 includes holes 322, insulator 304 includes holes 324, and reflector housing 306 includes holes 326 for receiving connectors therethrough.

In some embodiments, reflector unit 300 can be configured to at least partially surround print head 200. As illustrated in FIGS. 3A and 3B, in one embodiment, a central opening 308 may be defined in reflective plate 302, a central opening 310 may be defined in insulator 304, and a central opening 312 may be defined in reflector housing 306. Openings 308, 310, and 312 may be aligned such that they create one continuous opening when reflective plate 302, insulator 304, and reflector housing 306 are assembled. In some embodiments, openings 308, 310, and 312 may be configured to correspond to the shape of the distal end of print head 200. In some embodiments, a distal portion of print head 200 may pass through openings 308, 310, and 312 such that reflector unit 300 at least partially surrounds print head 200. As illustrated in FIG. 3A, in some embodiments, a distal end of print head 200 will extend out from reflector unit 300. In some embodiments, a distal portion of print head 200, which may include nozzle 210, is positioned below reflector unit 300.

In another embodiments, reflector unit 300 may be positioned adjacent to print head 200 and thus not require openings 308, 310, and 312. In such an embodiment, print head 200 does not pass through reflector unit 300. In some embodiments, there may be one or more reflector unit 300 and the reflector units 300 may be positioned adjacent to print head 200. In some embodiments comprising a plurality of reflectors 300, all reflector units 300 may not be active at the same time. Thus, each of the reflector units 300 can be independently controlled and independently operated. For example, in an embodiment comprising two reflector units 300, active heater 303 of a first reflector unit 300 may be energized and generate heat in an active state, while a second reflector unit 300 may include active heater 303 that is off and in a passive state. In such an example, although only the first reflector unit 300 is actively generating heat, both reflector units 300 are passively reflecting heat towards build plate 100.

In some embodiments, one or more active heaters 303 can be communicatively coupled to control system 50 for selectively controlling the parameters for active heater 303. As described in greater detail below, control system 50 may monitor and regulate the temperature and state (on/off) of active heater 303. For example, control system 50 may sense and monitor the temperature of printed object 800 and, depending on the sensed temperature, may energize or de-energize active heater 303 to control the heat directed towards printed object 800. For example if the temperature of printed object 800 is above a predetermined threshold, control system may de-energize active heater 303 to reduce the heat directed towards printed object 800. In some embodiments, control system 50 may be used to transmit manually inputted commands and may energize or de-energize active heater 303 in response to the manually inputted commands.

In some embodiments, reflector unit 300 may further comprise at least one cooling device or system (not shown) for cooling reflector unit 300. In some embodiments, cooling device may be located within reflector housing 306. In some embodiments, cooling device may be located externally on reflector housing 306. Cooling device may be configured as any known cooling device or system, such as a fan or a liquid cooling system. In some embodiments, cooling device may be communicatively coupled to control system 50. In some embodiments, control system 50 may automatically monitor and regulate cooling device. In some embodiments cooling device may be manually controlled by instructions and inputs entered into control system 50.

FIG. 5 is a perspective view of an embodiment of the interior of housing unit 12. In some embodiments, printing device 10 may further comprise at least one additional heat source. In some embodiments, the additional heat source may comprise at least one infrared (IR) light 500. It will be appreciated that IR light 500 could be replaced with any other known and suitable source for generating heat and is not intended to be a limiting feature. In some embodiments, IR light 500 may be positioned above build plate 100 and oriented to direct heat towards build plate 100. In some embodiments, IR light 500 may be attached and/or connected to housing unit 12. IR light 500 may be fastened to frame 14 or may be a stand-alone device located within interior of housing unit 12. In some embodiments, IR lights 500 may be attached to upper assembly 201 such that IR lights 500 are configured to move together with print head 200 and reflector unit 300. As can be seen in FIG. 5, one embodiment of printing device 10 comprises two opposing IR lights 500. In some embodiments, printing device 10 may comprise any number of IR lights 500. In some embodiments, IR light 500 may be communicatively coupled to control system 50 to selectively operate IR light 500. For example, control system 50 may be manually controlled to transition each IR light 500 from an off state to an on state. Alternatively, in some embodiments IR light 500 may be automatically controlled by control system 50 such that it is programmed to turn on or off based on predetermined parameters to maintain an optimized temperature of printed object 800 on build plate 100.

Figure 6:
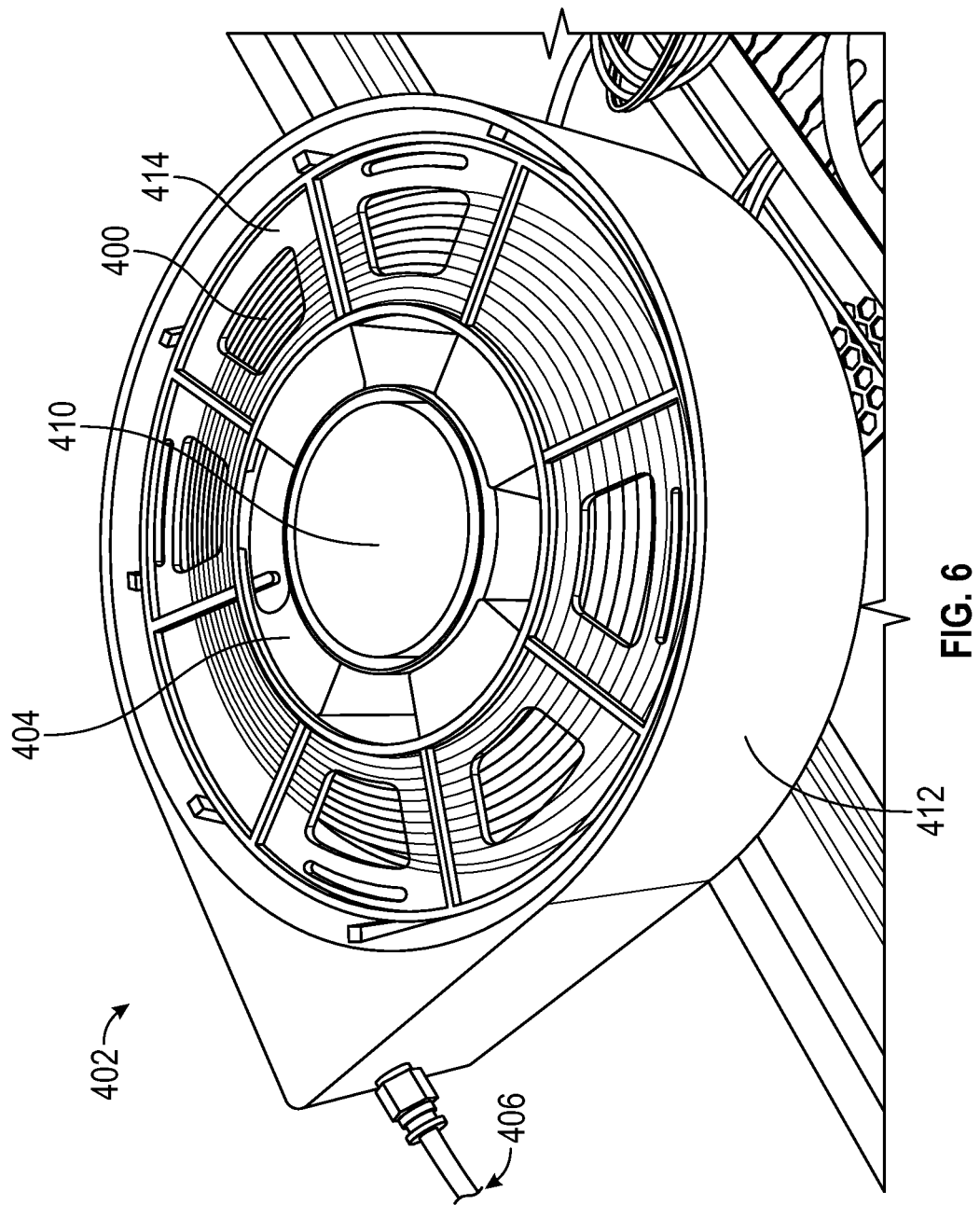
FIG. 6 is a perspective view of a material housing and printing material of the invention.

FIG. 6 is a perspective view of a material housing 402 for printing material 400 that may be used with printing device 10. Printing device 10 may be compatible with numerous printing materials including but not limited to high-performance polymers, such as PEEK, PAEK, PEKK, and/or combinations thereof. In some embodiments, printing material 400 may be in a filament form. Printing material 400 may comprise a range of diameters such as about 1 mm to about 5 mm in diameter.

In some embodiments, the printing material 400 may be implantable grade poly ether ketone rod stock, such as Vestakeep® i-Grade materials, Vestakeep® i4 R, or Vestakeep® i4 G resin. In some embodiments, the printing material 400 may be any medical grade FDA-approved material. In some embodiments, the printing material 400 may have a diameter of about 6-20 mm, about 25-60 mm or about 70-100 mm and a length of about 3000 mm, about 2000 mm, or about 1000 mm. In some embodiments, the printing material may be provided on a spool and have a length of about 60 mm or 160 mm and a diameter of about 1.75 mm. Printing material may be biocompatible, bistable, radiolucent, and sterilizable.

In some embodiments, printing material 400 may be housed in a material housing 402, which may be in the form of a spool, cylinder, or other suitable enclosure for the printing material 400. In one embodiment, material housing 402 can be a cylindrical housing unit comprising a filament spool 404 for rotatably receiving printing material 400 in a rotating manner. Spool has a central core 410 and side wall 412 for receiving the printing material 400 therebetween and a top cover 414. In some embodiments, printing material 400 may be wound around the central core 410 in a concentric manner.

In one embodiment, material housing 402 may be coupled to housing unit 12 by being mounted on frame 14. In one embodiment, material housing 402 may be coupled to one of the panels 16. In some embodiments, material housing 402 may be externally located, such as for example on a surface near printing device 10. In one embodiment, material housing 402 may be located on top of housing unit 12, either internally or externally. In some embodiments, material housing 402 can protect printing material from damage and heat. In some embodiments, material housing 402 may also help control the input of printing material 400 and prevent printing material 400 from unrolling on its own.

A distal end of the filament of printing material 400 extends from the material housing 402 to be receiving into feed tube 212 of print head 200. Printing material 400 can be conveyed to print head 200 by way of a transport device 406. Transport device 406 can provide a mechanical means for unspooling or otherwise transferring printing material 400 from material housing 402 to feed tube 212. In some embodiments, printing material 400 is conveyed to print head 200 via transport device 406 while printing material 400 is in a solid state. In some embodiments, transport device 406 may be configured as a mechanical extruder. Transport device 406 may have at least one operating state, for dispensing printing material 400 from material housing 402 to feed tube 212. The rate at which printing material 400 may be dispensed may be selectively controlled by control system 50. In some embodiments, printing material 400 may be dispensed at a rate of about 2 mm to about 20 mm per second. In some embodiments, printing material 400 may be dispensed at a faster or slower rate, which may vary during operation as desired. In some embodiments, transport device 406 may further be coupled to an extruder assembly 408. In some embodiments, extruder assembly 408 may comprise a motor, planetary gear, and extruder to provide a forward drive element to transport device 406 for feeding printing material 400 from material housing 402 to feed tube 212. Extruder assembly 408 can aid in ensuring that printing material 400 is fed to print head 200 in a consistent and reliable manner. Furthermore, extruder assembly 408 can aid in dispensing printing material 400 consistently and achieving a stable build during printing.

In some embodiments, printing device 10 may further include one or more temperature sensors for measuring the temperature within housing unit 12 at multiple locations. For example, sensor 510 may measure the temperature of build plate 100, sensor 244 may measure the temperature of printing material 400 within print head 200, sensor 242 may measure the temperature of nozzle 210 of print head 200. Sensors may be located at a plurality of positions within the interior of housing unit 12. In some embodiments, sensors may be located within build plate 100, print head 200, and/or reflector unit 300. Alternatively, in some embodiments, sensors may be located externally on build plate 100, print head 200, and/or reflector unit 300. In some embodiments, sensors may be used to measure the temperature of various elements in printing device 10. For example, sensors may be used to measure the temperature of printing material 400 at various points in the process, such as prior to reaching print head 200, at the print head 200, while printing material 400 is being dispensed, and after printing material 400 is received on top build layer 110. In some embodiments, sensors 510, 242, 244 may be thermistors or thermocouples. In some embodiments, sensors may be communicatively coupled to control system 50. For example, sensors could be used to measure the temperature of the current layer being printed of printed object 800 during printing. The measured temperature may then be transmitted to control system 50 and may be shown on display 52.

In some embodiments, printing device 10 may further comprise one or more cooling devices (not shown). In some embodiments, cooling devices may be one or more fans positioned within the interior of housing unit 12. In some embodiments, fans may be directionally oriented such that airflow may be directed towards build plate 100 and the printed object 800, thereby selectively cooling only build plate 100 and/or the printed object 800. Alternatively, in some embodiments, fans may be directionally oriented and positioned to direct airflow throughout the interior of housing unit 12, thereby providing ambient cooling of interior of housing unit 12, rather than specific cooling of selected locations. In some embodiments, cooling devices may comprise tubing located within housing unit 12 for liquid cooling. In some embodiments, tubing may be positioned at various points within housing unit 12, and may be used for cooling build plate 100, print head 200, reflector unit 300, and/or for cooling the interior of housing unit 12 generally. Tubing may be configured to receive water, liquid nitrogen, ethylene glycol/water mixture, propylene glycol/water mixture, or any other liquids that may be used in liquid cooling systems. In some embodiments, cooling devices may be communicatively coupled to control system 50. Control system 50 may be programmed to automatically control cooling devices and/or cooling devices may be manually controlled by instructions inputted into control system 50.

Figure 7:
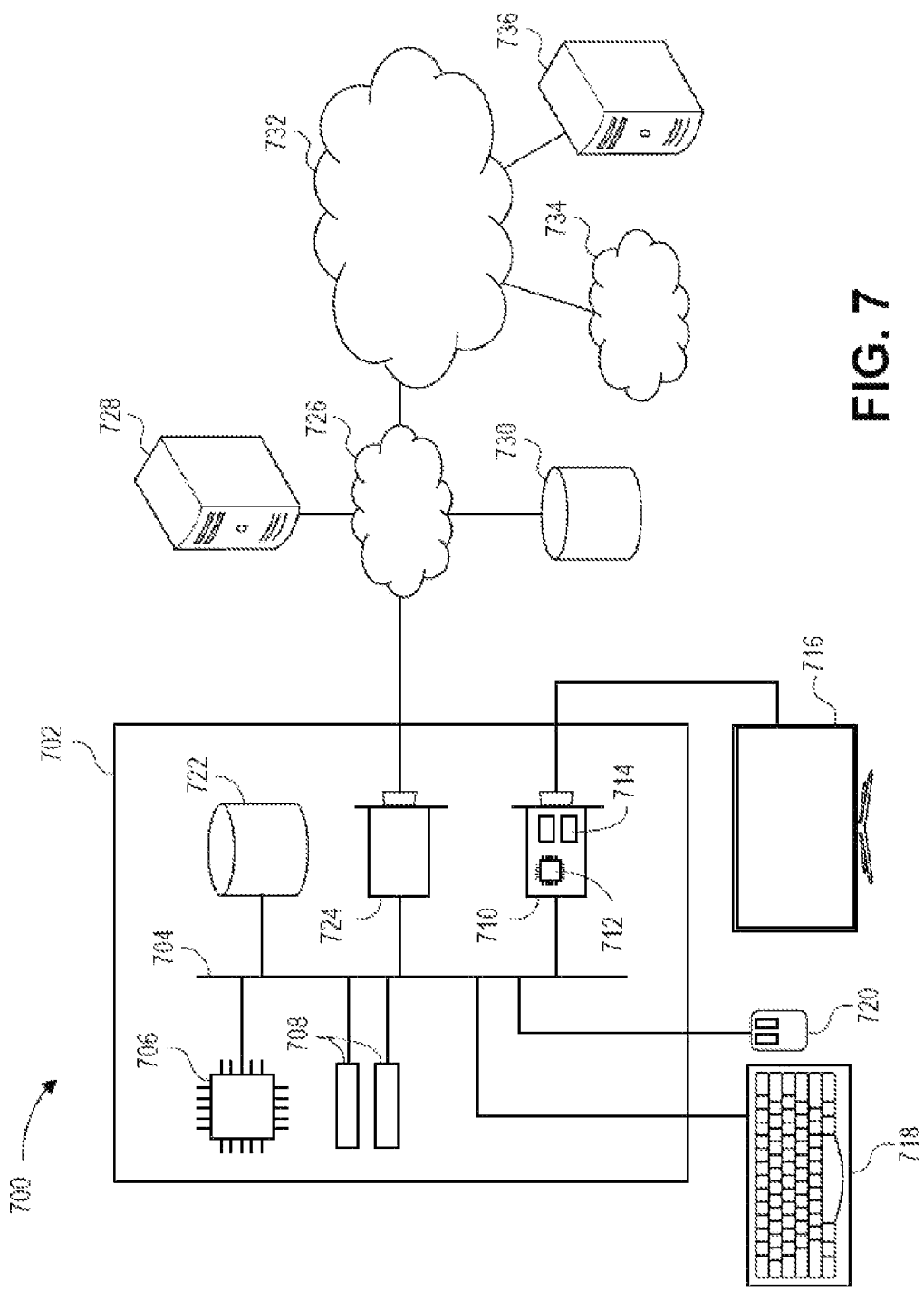
FIG. 7 depicts an exemplary hardware platform for certain embodiments of the invention.

FIG. 7 illustrates an exemplary computer hardware system 700, that may cooperate with printing device 10 and control system 50. Computing device 702 can be a desktop computer, a laptop computer, a server computer, a mobile device such as a smartphone or tablet, or any other form factor of general- or special-purpose computing device. Depicted with computing device 702 are several components, for illustrative purposes. In some embodiments, certain components may be arranged differently or absent. Additional components may also be present. Included in computing device 702 is system bus 704, whereby other components of computing device 702 can communicate with each other. In certain embodiments, there may be multiple busses or components may communicate with each other directly. Connected to system bus 704 is central processing unit (CPU) 706. Also attached to system bus 704 are one or more random-access memory (RAM) modules 708.

Also attached to system bus 704 is graphics card 710. In some embodiments, graphics card 710 may not be a physically separate card, but rather may be integrated into the motherboard or the CPU 706. In some embodiments, graphics card 710 has a separate graphics-processing unit (GPU) 712, which can be used for graphics processing or for general purpose computing (GPGPU). Also on graphics card 710 is GPU memory 714. Connected (directly or indirectly) to graphics card 710 is computer display 716 for user interaction. In some embodiments no display is present, while in others it is integrated into computing device 702. Similarly, peripherals such as keyboard 718 and mouse 720 are connected to system bus 704. Like computer display 716, these peripherals may be integrated into computing device 702 or absent. Also connected to system bus 704 is local storage 722, which may be any form of computer-readable media and may be internally installed in computing device 702 or externally and removably attached.

Finally, network interface card (NIC) 724 is also attached to system bus 704 and allows computing device 702 to communicate over a network such as network 726. NIC 724 can be any form of network interface known in the art, such as Ethernet, ATM, fiber, Bluetooth, or Wi-Fi (i.e., the IEEE 802.11 family of standards). NIC 724 connects computing device 702 to local network 726, which may also include one or more other computers, such as computer 728, and network storage, such as data store 730. Local network 726 is in turn connected to Internet 732, which connects many networks such as local network 726, remote network 734 or directly attached computers such as computer 736. In some embodiments, computing device 702 can itself be directly connected to Internet 732.

The computer program of embodiments of the invention comprises a plurality of code segments executable by a computing device for performing the steps of various methods of the invention. The steps of the method may be performed in the order discussed, or they may be performed in a different order, unless otherwise expressly stated. Furthermore, some steps may be performed concurrently as opposed to sequentially. Also, some steps may be optional. The computer program may also execute additional steps not described herein. The computer program, system, and method of embodiments of the invention may be implemented in hardware, software, firmware, or combinations thereof, which broadly comprises server devices, computing devices, and a communications network.

The computer program of embodiments of the invention may be responsive to user input. As defined herein user input may be received from a variety of computing devices including but not limited to the following: desktops, laptops, calculators, telephones, smartphones, smart watches, in-car computers, camera systems, or tablets. The computing devices may receive user input from a variety of sources including but not limited to the following: keyboards, keypads, mice, trackpads, trackballs, pen-input devices, printers, scanners, facsimile, touchscreens, network transmissions, verbal/vocal commands, gestures, button presses or the like.

The monitor, server devices, and computing devices 702 may include any device, component, or equipment with a processing element and associated memory elements. The processing element may implement operating systems, and may be capable of executing the computer program, which is also generally known as instructions, commands, software code, executables, applications ("apps"), and the like. The processing element may include processors, microprocessors, microcontrollers, field programmable gate arrays, and the like, or combinations thereof. The memory elements may be capable of storing or retaining the computer program and may also store data, typically binary data, including text, databases, graphics, audio, video, combinations thereof, and the like. The memory elements may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), and the like, or combinations thereof. In addition to these memory elements, the server devices may further include file stores comprising a plurality of hard disk drives, network attached storage, or a separate storage network.

The computing devices may specifically include mobile communication devices (including wireless devices), workstations, desktop computers, laptop computers, palmtop computers, tablet computers, portable digital assistants (PDA), smartphones, and the like, or combinations thereof. Various embodiments of the computing device may also include voice communication devices, such as cell phones and/or smartphones. In preferred embodiments, the computing device will have an electronic display operable to display visual graphics, images, text, etc. In certain embodiments, the computer program facilitates interaction and communication through a graphical user interface (GUI) that is displayed via the electronic display. The GUI enables the user to interact with the electronic display by touching or pointing at display areas to provide information to the monitor.

The communications network may be wired or wireless and may include servers, routers, switches, wireless receivers and transmitters, and the like, as well as electrically conductive cables or optical cables. The communications network may also include local, metro, or wide area networks, as well as the Internet, or other cloud networks. Furthermore, the communications network may include cellular or mobile phone networks, as well as landline phone networks, public switched telephone networks, fiber optic networks, or the like.

The computer program may run on computing devices or, alternatively, may run on one or more server devices. In certain embodiments of the invention, the computer program may be embodied in a stand-alone computer program (i.e., an "app") downloaded on a user's computing device or in a web-accessible program that is accessible by the user's computing device via the communications network. As used herein, the stand-alone computer program or web-accessible program provides users with access to an electronic resource from which the users can interact with various embodiments of the invention.

In some embodiments, prior to the printing process, the object data corresponding to an object 800 to be printed can be transmitted to control system 50, which may cooperate with or include computing device 702. In some embodiments, the object data may be transmitted to control system 50 in file formats such as .stl, obj. or .amf, or any other file format created by a computer-aided design (CAD) program or software. In some embodiments, the object data may include the geometry of the object 800 to be printed as well as additional information such as tolerances, expansions, strength properties, etc. Subsequently, the CAD data may be divided up into individual layers, such as by means of a slicer program or software. Accordingly, the slicer software may transform the 3D model of the CAD software into a readable format for control system 50. In this regard, division into layers can take place both externally and in printing device 10 itself. In some embodiments, before the printing process, a shrinkage process of the printed object during cooling after a printing process may be calculated. The print routine of the individual layers can be translated into machine readable code and transmitted to control system 50. In some embodiments, the software of control system 50 can be a web-based application. In some embodiments, the software of control system 50 can be a computer-based software program.

In some embodiments, the object data transmitted to printing device 10 may be a generic, or otherwise non-custom designs for objects 800. Such designs may be useful for mass production products or when the printed object 800 will be repeatedly printed. In some embodiments, the object data may be for creating a specific, custom, or one-of-a-kind object, wherein the printed object 800 will be a uniquely designed.

For example, in some embodiments, printing device 10 may be used to print objects 800 such as medical devices or surgical implants, including spinal implants, maxillo-facial implants, ankle or foot wedges, or cranial plates. Implants that are designed to be patient-specific and are custom-made may have increased effectiveness. Such implants may be custom designed and configured to match the anatomy of a specific patient and may be configured to be printed on-site. Computer modeling may be used for obtaining three-dimensional images of the specific patient's anatomy through the use of MRI or CT scans, and designs, parameters, and other object data information may be constructed and designed using various CAD programs or software. Accordingly, in some embodiments, the object data may comprise unique and patient specific instructions for printing a patient-specific object 800, such as a surgical implant.

Figure 8A:
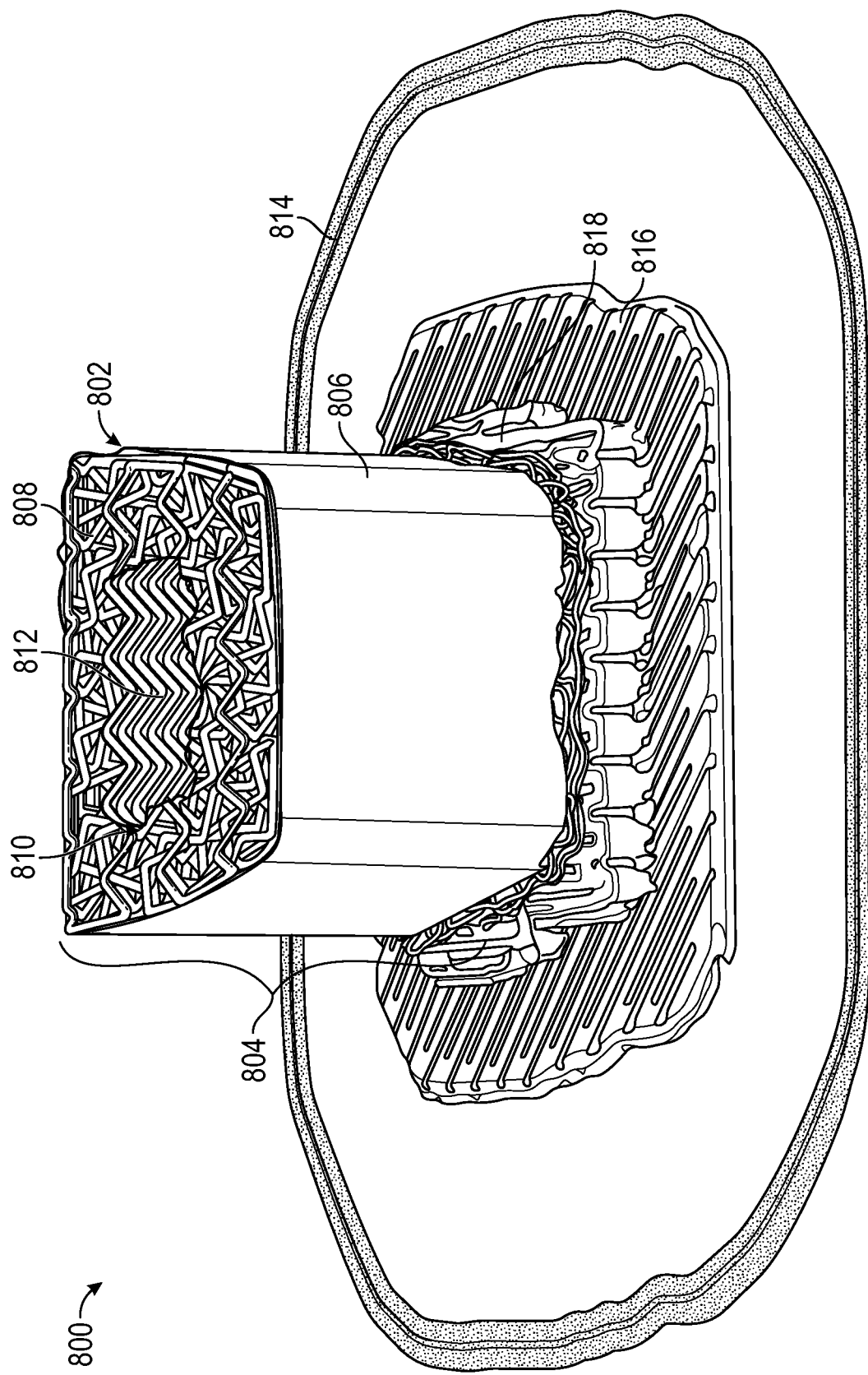
FIG. 8A is a perspective view of an embodiment of a printed object that may be printed by the printing device of the invention.

FIG. 8A illustrates an exemplary embodiment of a printed object 800 that may be printed using a FFF process with printing device 10. Printed object 800 may comprise a medical implant 802, a raft 816, and a scaffolding 818. Implant 802 may comprise a plurality of layers 804, a first porous region 806, a second porous region 808 having a lattice work structure 810, and a void 812. Raft 816 may be a printed structure, printed directly on top build layer 110 and which acts as a barrier between direct contact of medical implant 802 and top build layer 110. Raft 816 may further reduce or limit the frequency of warping or crystallization of medical implant 802. Raft 816 creates an interface between the implant and the top build layer 110. Raft 816 is composed of the same material as the implant 800. In some embodiments, raft 816 may be composed of about three printed layers on top of one another. The printing material in the raft 816 may be loosely spaced and is simply to provide structure to build the implant 802 upon.

As described in greater detail below, printed object 800 may further comprise a scaffolding 818. In some embodiments, scaffolding 818 may be used to create a level build plane for medical implant 802, such that when each layer of the plurality of layers 804 is printed, printing material 400 is dispensed on a generally horizontal and level plane. Scaffolding 818 may be broken away once the implant 802 is finished and ready for use. In some embodiments, the scaffolding 818 may be have a slanted top surface, such as when it is desired for the bottom surface of the implant 802 to be tapered. The top surface of the scaffolding 818 may be slanted at a particular angle, such as 7 degrees to about 45 degrees, however any angle may be used as desired. Thus, the orientation of the implant 802 may change based on the shape of the scaffolding 818.

In some embodiments and as described in greater detail below, a test circle 814 may be printed prior to printing printed object 800 to ensure that printing material 400 is being dispensed at the correct consistency and flow rate.

After receiving the object data of a printed object 800, printing device 10 may begin the printing process. As stated above, printing device 10 may be used in a variety of additive manufacturing processes including without limitation FFF printing.

Figure 9:
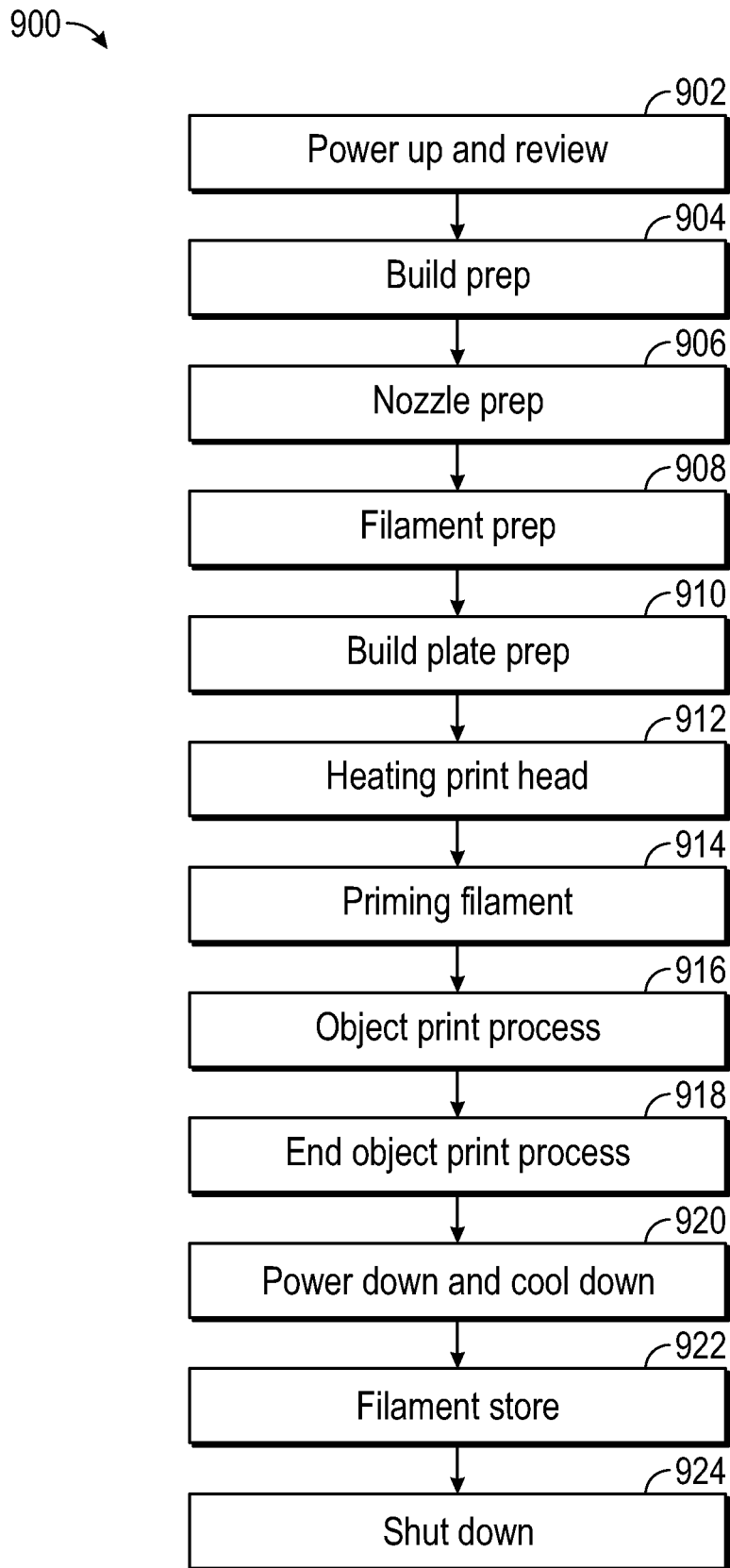
FIG. 9 is an exemplary flowchart illustrating a method of using the printing device of the invention.

FIG. 9 illustrates one embodiment of a method 900 of using printing device 10 to print printed object 800. A first step in method 900 may comprise a power up 902 and review step. Power up 902 may comprise diagnostics of control system 50 and the user interface, web-based application, or program, ensuring that control system 50 is working properly. Power up 902 may further include a review of a network status of control system 50, a review of lower drive train 124 and upper drive train 280, and a review of an ambient temperature within housing unit 12.

A second step of method 900 may further include a build prep 904 step. For example, during build prep 904 a cleaner may be used to clean top build layer 110 of build plate 100 in order to prepare the surface of top build layer 110 to receive printing material 400. In some embodiments, the cleaner may be an acetone cleaner. Build prep 904 may further include wiping top build layer 110 with a lint-free cloth and isopropyl alcohol.

A third step of method 900 may include a nozzle prep 906 step. During nozzle prep 906, print head 200 may be inspected and reviewed to ensure that it is prepared for printing. For example, during nozzle prep 906 feed tube 212 may be inspected for debris or other blockages, such as leftover printing filament 400 from a previous printing. For example, in an embodiment in which printing filament 400 is comprised as PEEK, print head 200 may be heated to about 350° C. to melt any leftover PEEK that may be blocking feed tube 212. Print head 200 may further be cleaned with a cleaner, such as a cotton swab.

A fourth step of method 900 may include a filament prep 908 step. In some embodiments, printing material 400 may comprise a material that is either dangerous to touch with a bare hand or would otherwise lose effectiveness is touched by a bare hand. Therefore, it may be advantageous to load printing material 400 into material housing 402 using nitrile, or other sterile gloves. Printing filament 400 may then be partially unspooled, or otherwise fed into transport device 406. In some embodiments, there may be printing material 400 that is at least partially exposed to air, or otherwise not contained within material housing 402. The exposed printing material 400 may further be cleaned, wiped, or otherwise prepped with isopropyl alcohol or another cleaner, to aid in maintaining purity of printing material prior to printing. During filament prep 908, printing material 400 may be cut to a predetermined length.

A fifth step of method 900 may include a build plate prep 910 step. In some embodiments, build plate 100 may be pre-heated to a predetermined temperature. In some embodiments, the predetermined temperature may be based on the specific composition of printing material. For example, in some embodiments, printing material 400 may comprise a PEEK filament, printed using a FFF method of additive manufacturing. In such an embodiment, build plate 100 can be preheated to about 145° C. Pre-heating build plate 100 to about 145° C. can help to prevent warpage of top build layer 110 and/or help prevent crystallization of printed object 800 during printing. Build plate 100 may alternatively be pre-heated to a range of temperatures, depending on the embodiment and the composition of printing material 400. In some embodiments, build plate 100 may be preheated to a temperature of about 50° C. to about 350° C. It will be appreciated that depending on the embodiment, build plate 100 may be pre-heated to any temperature required for additive manufacturing. Build plate may be pre-heated using the heating layer 106, the reflector unit 300, and/or the IR lights 500.

A sixth step of method 900 may include a heating print head 912 step. In some embodiments, print head 200 may be pre-heated to a temperature that is hot enough to melt printing material 400, and transition printing filament 400 from a solid state to a liquid or molten state. For example, in some embodiments, printing material 400 may comprise a PEEK material and print head 200 may be pre-heated to about 450° C. to melt the PEEK for dispensing. In some embodiments, print head 200 may be heated to a temperature that transitions printing filament 400 from a solid state to a glossy state, whereby print head 200 can be heated to a temperature that is able to maintain printing material 400 at or near a glass transition state.

A seventh step of method 900 may include priming filament 914. During priming filament 914, a pre-determined amount of printing material 400 can be transported from material housing 402 to feed tube 212 and dispensed out from nozzle 210 onto top build layer 110. In some embodiments, the predetermined amount of material 400 may be dispensed out into a test circle 814, for example, or as a line or other shape. Test circle 814 may be used as a test to determine whether the flow and dispensing of printing material is at an acceptable level, ensuring that the flow of printing material 400 is even and at a desired dispensing speed.

An eighth step of method 900 may include an object print process 916 step. During object print process, lower drive train 124, upper drive train 280, build plate 100, print head 200, reflector unit 300, IR lights 500, sensors 242, 244, 510, and any other component of printing device 10 that is communicatively coupled to control system 50 can be controlled by control system 50. The temperature of print head 200, the temperature of printing material 400, the position of build plate 100, and other pertinent parameters can be displayed on display 52 during object print process 916. During object print process 916, object data for a specific printed object 800 can be selected and uploaded or transmitted to control system 50, whereby the design, parameters, and other information comprising the object data may be used for mapping or setting the printing pattern of printed object 800. As discussed in greater detail below, in some embodiments G-code or software executed by control system 50 can break down a 3-D model of printed object 800 into slices or a plurality of layers, wherein a printing pattern can be implemented for each slice or layer.

During object print process 916, printing material 400 may be continuously fed through feed tube 212 and continuously dispensed from nozzle 210. The rate at which printing material 400 is fed through feed tube 212 and dispensed from nozzle 210 may be monitored and regulated by control system 50. Accordingly, control system 50 may be used to increase or decrease the rate at with dispensing material 400 is fed through feed tube 212. It will be appreciated that during object print process 916, the rate at which printing material 400 is fed through feed tube 212 or dispensed from nozzle 210 may fluctuate. In some embodiments, as printing material 400 is fed through feed tube 212 and reaches heater 206, printing material 400 may be heated and melted so that it can be dispensed out from nozzle 210. After melting, printing material 400 can then be dispensed from nozzle 210 onto the pre-heated top build layer 110.

In some embodiments, printing material 400 may be used to print a raft 816 on top build layer 110, prior to printing implant 802. Raft 816 may be printed on top build layer 110 and act as either a stabilizer, buffer layer, or protection layer providing a barrier between printed implant 802 and top build layer 110, preventing direct contact between printed implant 802 and top build layer 110. Accordingly, raft 816 may comprise a dimension that is larger than the dimensions of printed implant 802, wherein raft 816 prevents any direct contact between printed implant 802 and top build layer 110. Raft 816 may have a surface that is larger than the surface of printed object 800, wherein printed implant 802 is printed entirely on the surface of raft 816 and does not come into contact with top build layer 110. In some embodiments, raft 816 may comprise a generally elliptical shape. In some embodiments raft 816 may comprise any geometric shape, and for example, may be circular, triangular, rectangular, pentagonal, or any polygonal shape. In some embodiments, printed implant 802 may be printed directly on raft 816 rather than on top build layer 110. In some embodiments, raft 816 may be removed from printed implant 802 after object print process 916 has been completed. For example, in some embodiments raft 816 may only be required only during object print process 916.

In some embodiments, printing material 400 may be used to print scaffolding 818, prior to printing implant 802. Scaffolding 818 may be used to print a leveling plane or structure to aid in maintaining printed implant 802 at a level, or approximately horizontal build-plane. For example, in some embodiments printed implant 802 may be printed having a varying angle or approximation of the angle of each layer of the plurality of build layers. Accordingly, scaffolding 818 may be printed and comprise a plurality of layers comprising different levels or angles wherein implant 802 may be printed upon. The levels or angles of scaffolding 818 may be used to provide a structure or base level wherein each layer of implant 802 may be printed at an approximately horizontal plane. Scaffolding 818 may be particularly advantageous when implant 802 comprises a slanted or angled design, wherein each layer of implant 802 may be printed at approximately a horizontal level or plane. Scaffolding 818 may comprise a plurality of layers, depending on the embodiment, to provide a level build plane for implant 802. The plurality of layers of scaffolding 818 may comprise varying heights or dimensions, depending on the dimensions and final height of implant 802. The dimensions of scaffolding 818 may vary, and in some embodiments may have a dimension that is larger than the dimensions of implant 802. Alternatively, in some embodiments the dimensions of scaffolding 818 may have be equal to the dimensions of implant 802. Alternatively, in some embodiments the dimensions of scaffolding 818 may be smaller than the dimensions of implant 802.

Thus, an exemplary object print process 916 may comprise printing raft 816 on top of the build plate 100, printing a scaffolding 818 on top of the raft 816, and printing the implant 802 on top of the scaffolding 818. Furthermore, implant 802 may be printed in a plurality of layers, with each layer being completed before the next layer is begun. For example, in some embodiments a first printed layer may be printed in a pre-determined pattern, thickness, or other parameters. In some embodiments, a first layer of implant 802 may be printed in its entirety before moving up in the z-plane and printing of a second layer begins. In some embodiments, printing material 400 can be contiguously dispensed from nozzle 210, wherein implant 802 comprises a near constant or contiguous composition, void of gaps, breaks, or spaces in the dispensed printing material. Alternatively, in some embodiments printing material 400 can be dispensed as droplets or in an otherwise non-contiguous flow from nozzle 210.

In some embodiments, after a first layer has been completed, a second layer of implant 802 can begin to be printed. In some embodiments, build plate 100 may be moved down in the z-plane via lower drive train 124, moving top build layer 110 and partially printed implant 802 further away from print head 200. Accordingly, as implant 802 is moved away from print head 200, printing material 400 can be dispensed on top of the printed first layer. In some embodiments build plate 100 may remain static and print head 200 may be moved directionally in the z-plane. For example, after dispensing a first layer of printed object 800, upper drive train 280 can be used to directionally move print head 200 up in the z-plane, further away from build plate 100. In some embodiments, either or both of build plate 100 and print head 200 may be directionally moved in the z-plane during printing.

An exemplary method for forming a porous surgical device by contiguous deposition may include providing a printing material 400 comprised of a filament material and forming a first layer of the surgical device by depositing the printing material 400 on a top surface of a build plate 100. Forming the first layer may include the step of extruding the printing material through a nozzle 210 beginning at a first X-Y position relative to the top surface of the build plate, wherein the first layer is formed by depositing the printing material 400 in a substantially contiguous pattern to form at least a first region of the porous surgical device, wherein the first region has a first porosity. A further step comprises forming a second layer of the surgical device by moving the print head 200 in a Z-plane to a second Z-plane position and extruding the printing material 400 through the nozzle 210 beginning at a second X-Y position relative to the top surface of the build plate 100, wherein the second X-Y position is a predetermined distance or angle from the first X-Y position. Additional layers may be formed by moving the nozzle head in the Z-plane relative to a prior Z-plane position, extruding the printing material 400 through the nozzle 210 beginning at an X-Y position relative to the surface of the build plate 100, wherein the X-Y position for any one of the plurality of layers is a predetermined distance or angle from any prior X-Y position. Any one of the plurality of layers may have a region having a porosity that is smaller or larger than any prior-formed layer. Additionally, the porosity of each layer may vary within the layer itself.

In some embodiments, it may be advantageous or necessary to heat printed object 800 during object print process 916. For example, in some embodiments printing material 400 may consist of a filament material, such as PEEK, PAEK, or PEKK for example. In some embodiments, printing material 400 may be prone to crystallization, warping, or other problematic instances caused by the temperature within housing unit 12 being too low or too high. Therefore, it can be advantageous to maintain a temperature range within housing unit 12 that will prevent or limit the frequency of printing material 400 crystalizing or warping. For example, prior to dispensing printing filament 400, top build layer 110 may be preheated to about 140° C. to about 160° C., and the temperature may be maintained during the entirety of object print process 916. Sensors 510 located internally within build plate 100 or sensors located externally to build plate 100 may measure the temperature of top build layer 110, and control system 50 may actively monitor and regulate the temperature of top build layer 110. The heat generated from build plate 100 and subsequent heating of top build layer 110 can provide heat to printed object 800. The generated heat can aid in preventing crystallization or warping of printed object 800 during object print process.

In some embodiments, heat generated by reflector unit 300 can further aid in preventing crystallization or warping. During object print process 916, sensors located within housing unit 12 can measure the temperature of printed object 800, including the temperature of one or more layers of printed object 800. It will be appreciated that in some embodiments, it may be advantageous to selectively heat printed object 800 rather than creating a static heating environment within housing unit 12. For example, as each layer of printed object 800 is dispensed and formed, the temperature of each layer, or a plurality of layers, can be measured. The measured temperature can be transmitted to control system 50, whereby control system 50 can instruct active heater 303 of reflector unit 300 to generate more or less heat to printed object 800. In some embodiments, control system 50 can further instruct IR lights 500 to generate more or less heat to printed object 800. In some embodiments, it may be advantageous to keep or maintain printed object 800 or its layers, near or at a glass transition state to prevent crystallization or warping and keep printed object 800 at a glossy state during object print process 916. Therefore, control system 50 can continually monitor the temperature of printed object 800 or its layers and maintain the temperature by sending instructions to reflector unit 300 and/or IR lights 500. In some embodiments, as printed object 800 is moved further away from reflector unit 300 and/or IR lights 500 may be energized at a higher level to increase the generated heat directed to printed object 800. It will be further appreciated that in addition to, or alternatively as a sole means of temperature control, reflector unit 300 and bottom surface 314 may also reflect heat generated from heating layer 106 back towards printed object 800. Accordingly, it will be appreciated that during object print process 916 printed object 800 may be heated from below by heating layer 106 of build plate 100 and/or from above by reflector unit 300 (either actively through active heater 303 or passively by reflective bottom surface 314) and/or IR lights 500.

In some embodiments, control system 50 can monitor the temperature of printed object 800 during object print process 916, and through the heating elements within housing unit 12, can maintain a pre-determined temperature of printed object 800. For example, in some embodiments printing material 400 may comprise a PEEK filament. It may be determined that a printed object 800 made from PEEK filament is required to be maintained within a range of about 140° to about 160° C. during object print process 916. Sensors within housing unit 12 may measure the temperature of printed object 800 and transmit that information to control system 50, which can further send instructions to active heating elements (active heater 303, heating layer 106, IR lights 500) within housing unit 12 to maintain the temperature of printed object 800 within the determined range. For example, as printed object 800 is moved further away from print head 200 as object print process 916 progresses, control system 50 may send instructions to active heater 303 to energize and direct more heat to printed object 800.

In some embodiments, the thickness of the dispensed printing material 400 may be controlled by the rate at which printing material 400 is dispensed from print head 200. For example, in some embodiments, the thickness of the dispensed printing material 400 can inversely corresponded to the flow rate at which printing material 400 is dispensed. Thus, the bead of printing material 400 dispensed at 10 mm per second will be thinner than a bead of printing material 400 dispensed at 8 mm per second. In some embodiments, the flow rate and dispensing speed of printing material 400 can be selectively controlled by control system 50 and in accordance with the object data.

In some embodiments, the thickness of the dispensed printing material 400 may be controlled by the rate at which build plate 100 is moved in the x-y plane. For example, in some embodiments, if the flow rate of printing material 400 is kept constant, the thickness of the dispensed printing material 400 can inversely correspond to the acceleration or deceleration of build plate 100 in the x-y plane. Thus, the bead of printing material 400 dispensed on build plate 100 moving at 12 mm per second will be thinner than a bead of printing material 400 dispensed on build plate 100 moving at 8 mm per second. In some embodiments, the acceleration or deceleration of build plate 100 in the x-y plane can be selectively controlled by control system 50 and in accordance with the object data.

In some embodiments, the flow rate of printing material 400 dispensed from print head 200 may be synchronized with the rate at which build plate 100 is moved in the x plane and/or y plane. For example, in some embodiments, printing material 400 may be dispensed at a constant rate to achieve a constant and uniform bead thickness and build plate 100 may be moved in the x-y plane at the same speed that printing material 400 is dispensed from print head 200. For example, in some embodiments, if printing material 400 is dispensed at 10 mm per second, a consistent and uniform bead thickness can be achieved if build plate 100 is moved in the x-y plane at 10 mm per second. In some embodiments, there may be variance between the flow rate of printing material 400 dispensed from print head 200 and the speed that build plate 100 is moved in the x plane and/or the y plane. For example, in some embodiments the variance between the flow rate of the printing material 400 and the speed of build plate 100 may vary in increments of about 2 mm/second. For example, if printing material 400 is dispensed at a constant rate of 10 mm/second, to achieve a thicker bead size, build plate 100 may be moved at about 8 mm/second in the x-y plane. Conversely, if printing material 400 is dispensed at a constant rate of 10 mm/second, to achieve a thinner bead size, build plate 100 may be moved at about 12 mm/second in the x-y plane. Alternatively, the same effect may be achieved by moving build plate 100 at a constant speed in the x-y plane and varying the flow rate of printing material 400.

It will be appreciated that the flow rate and dispensing speed of printing material 400 may fluctuate or vary during object print process 916. For example, in some embodiments, printed object 800 may comprise layers or sections of varying thicknesses or sizes, requiring multiples sizes and thicknesses of dispensed printing material 400. Accordingly, the flow rate and dispense rate of printing material 400 may be regulated so that printing material 400 is dispensed at the correct size and thickness at the correct position.

A ninth step of method 900 may comprise an end object print process 918. For example, after the final layer of printed object 800 has been dispensed, printed object 800 may be removed from top build layer 110. In some embodiments, after removing printed object 800 from top build layer 110, raft 816 may be removed from printed implant 802. In some embodiments, scaffolding 818 may also be removed from implant 802. As described in greater detail herein, after removing scaffolding 818 and/or raft 816, implant 802 may be cleaned or sterilized.

A tenth step of method 900 may comprise a power down and cooldown 920 step. During power down and cooldown 920, heating element 114, heater 206, active heater 303, IR lights 500, and/or any other heated component of printing device 10 may be turned off and cooling may begin. The temperature of printing device 10 and the various heating elements may be monitored by sensors and control system 50. In some embodiments power down and cooldown 920 may be expedited by one or more coolers, such as fans or liquid coolers.

An eleventh step of method 900 may comprise a filament store 922 step. Any excess printing material 400 may be removed from material housing 402 and stored in a storage unit (not shown). In some embodiments, printing material 400 may comprise a material that is either dangerous to touch with a bare hand or would otherwise lose effectiveness if touched by bare hands. Therefore, it may be advantageous to remove printing material 400 from material housing 402 using nitrile, or other sterile gloves. Printing material 400 may be stored in a dry storage unit to prevent moisture or other contamination, which may limit the effectiveness of printing material 400 for future uses.

A twelfth step of method 900 may comprise a shut down 924 step. During shut down 924, control system 50 may be turned off or shut down. Printing device 10 may further be power downed or shut off. This may include unplugging printing device 10 from a power source or removing a battery or other energy source from printing device 10.

With respect to FIGS. 8A-8E, in some embodiments, printing device 10 may be used to print or create printed objects 800 having one or more porous regions, each having a different porosity. For example, FIG. 8A illustrates one embodiment of printed object 800, where printed object 800 comprises a medical implant 802. Implant 802 is composed of a plurality of layers 804 that create at least a first porous region 806 and a second porous region 808. It will be appreciated that in alternate embodiments, medical implant 802 may comprise one, two, or more different porous regions. In some embodiments, medical implant 802 may be a patient-specific or custom-made implant, that is designed for a specific patient and modeled on that particular patient's anatomy using computer-aided design software. Alternatively, in some embodiments medical implant 802 may comprise a generic design that is not custom or patient-specific. While references herein refer to printed object 800 as a medical implant, it will be appreciated that printing device 10 is not intended to be limited to printing objects for use in the medical or surgical field. Accordingly, printing device 10 may be used to print or construct any type of object 800 that can be formed through additive manufacturing.

In some embodiments, medical implant 802 may comprise a plurality of layers 804, wherein each layer within the plurality of layers 804 comprises both a first porous region 806 and a second porous region 808. In some embodiments, medical implant 802 may be printed layer-by-layer, wherein the entirety of one layer is printed prior to starting printing of the next layer. This process can be repeated until each layer has been printed and medical implant 802 is completely formed.

In some embodiments, after the object data of medical implant 802 is uploaded to control system 50, a three-dimensional model of medical implant 802 may be mapped by control system 50, which may be programmed with a G-code or other software, and a printing pattern may be implemented. For example, in some embodiments the three-dimensional model of medical implant 802 may be broken down or paired down to a plurality of layers or slices, thereby transitioning the three-dimensional model into a two-dimensional representation of what the printing footprint will comprise. For example, a 3-D model of medical implant 802, or any other object, may be uploaded to control system 50. Starting from the top of the 3-D model, the G-code or software can begin breaking or pairing down the 3-D model into slices or layers. In some embodiments, the slices may be about 50 µm to about 250 µm in thickness, and may depend on the printing material used. The G-code or software can then map or design a printing pattern for depositing printing material 400 for ultimately forming medical implant 802. In some embodiments, the G-code or software can further set or define the outer boundary or perimeter 844. During printing, printing material 400 may be deposited in the pattern mapped out by the G-code or software. In some embodiments, the G-code or software can further map or design the location of first porous region 806 and/or second porous region 808. In some embodiments, the printing pattern or porosity may be altered between each slice, providing for multiple printing patterns and porosities within the fully formed medical implant 802.

Figure 8B:
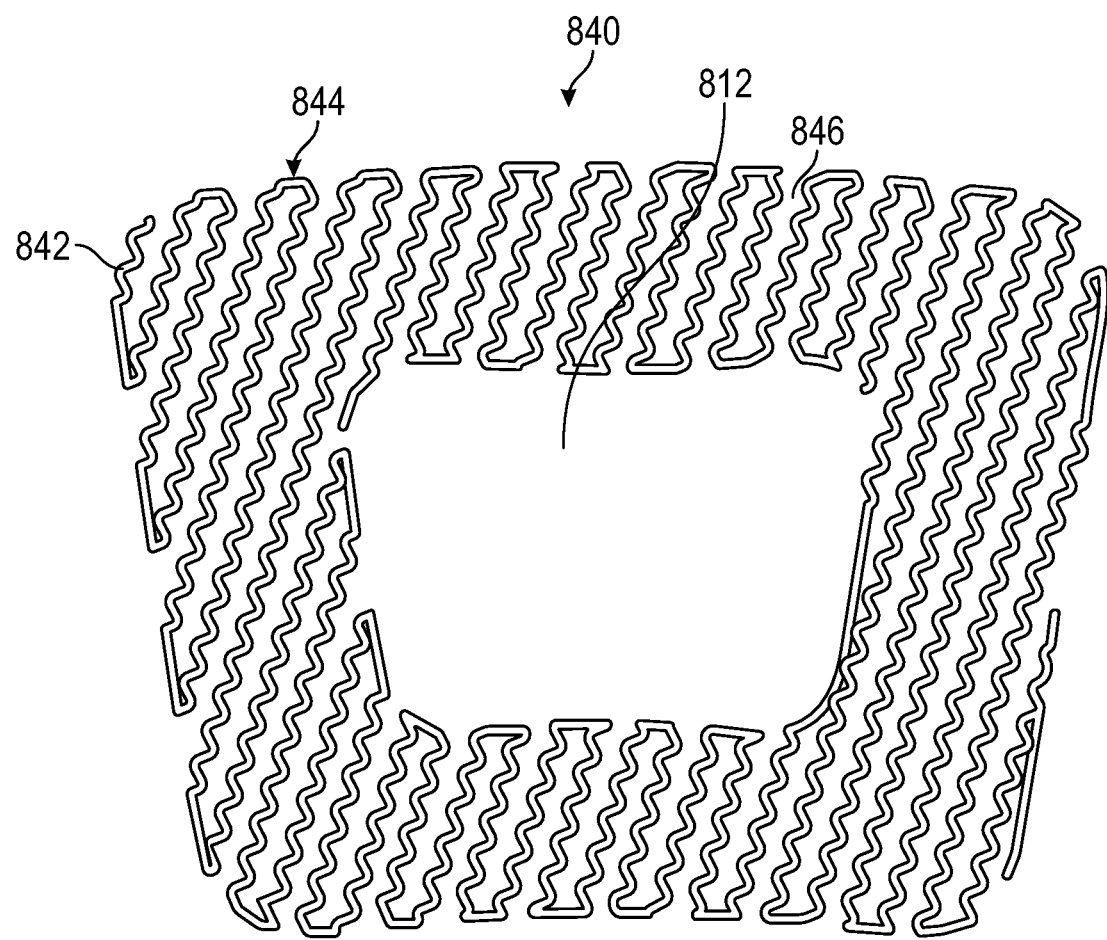
FIG. 8B is a perspective view of a first layer of an exemplary embodiment of the printed object.

FIG. 8B illustrates an exemplary embodiment of a first layer 840 of the plurality of layers 804. As illustrated, in some embodiments, first layer 840 may be formed from printing material 400 that is dispensed in a wave, zigzag, serpentine, curved, or other pattern. In some embodiments, printing material 400 may be dispensed in a singular straight-line pattern. FIG. 8B illustrates an exemplary embodiment of first layer 840 wherein printing material is dispensed in a wave-like sinusoidal pattern 842. As seen in FIG. 8B, in some embodiments, wave pattern 842 may be dispensed in a near contiguous or continuous manner. As such, printing material 400 may be dispensed from print head 200 at a substantially continuous or contiguous rate. For example, when printing material is dispensed 400, it can be dispensed nearly continuously to avoid gaps, breaks, or an otherwise disruption of dispensing. Accordingly, wave pattern 842 can comprise a generally contiguous and solid bead of printing material 400, absent any breaks or gaps. In some embodiments, printing material 400 can be dispensed beginning at a first x-y position, relative to top build layer 110. Printing material 400 can be contiguously dispensed in wave pattern 842 and moved in the x-y plane until reaching a predetermined perimeter 844 defining the outer dimension of medical implant 802. In some embodiments, upon reaching perimeter 844, print head 200 can be moved in the x-y plane and continue depositing printing material in wave pattern 842 back in the direction towards the interior of medical implant 802 until reaching perimeter 844 again. In some embodiments, there may be a multiple gaps 846 or spaces between printing material 400 deposited in wave pattern 842. For example, in some embodiments gaps 846 may be about 300 µm. In some embodiments, gaps 846 may be selected from a range of about 50 µm to about 500 µm. As further illustrated in FIG. 8B, printing material 400 may be contiguously deposited in wave pattern 842, turning back to the interior each time perimeter 844 is reached until first layer 840 is completed. Upon completion of first layer 840, depositing of second layer 850 may begin. In some embodiments, printing material 400 may be contiguously printed after each layer is completed, such that there is no gap or space of printing material between each layer, resulting in a contiguous or nearly contiguous medical implant 802. For example, after completing first layer 840, depositing of second layer 850 may begin without stopping the feed of printing material 400 through feed tube 212 from nozzle 210.

Figure 8C:
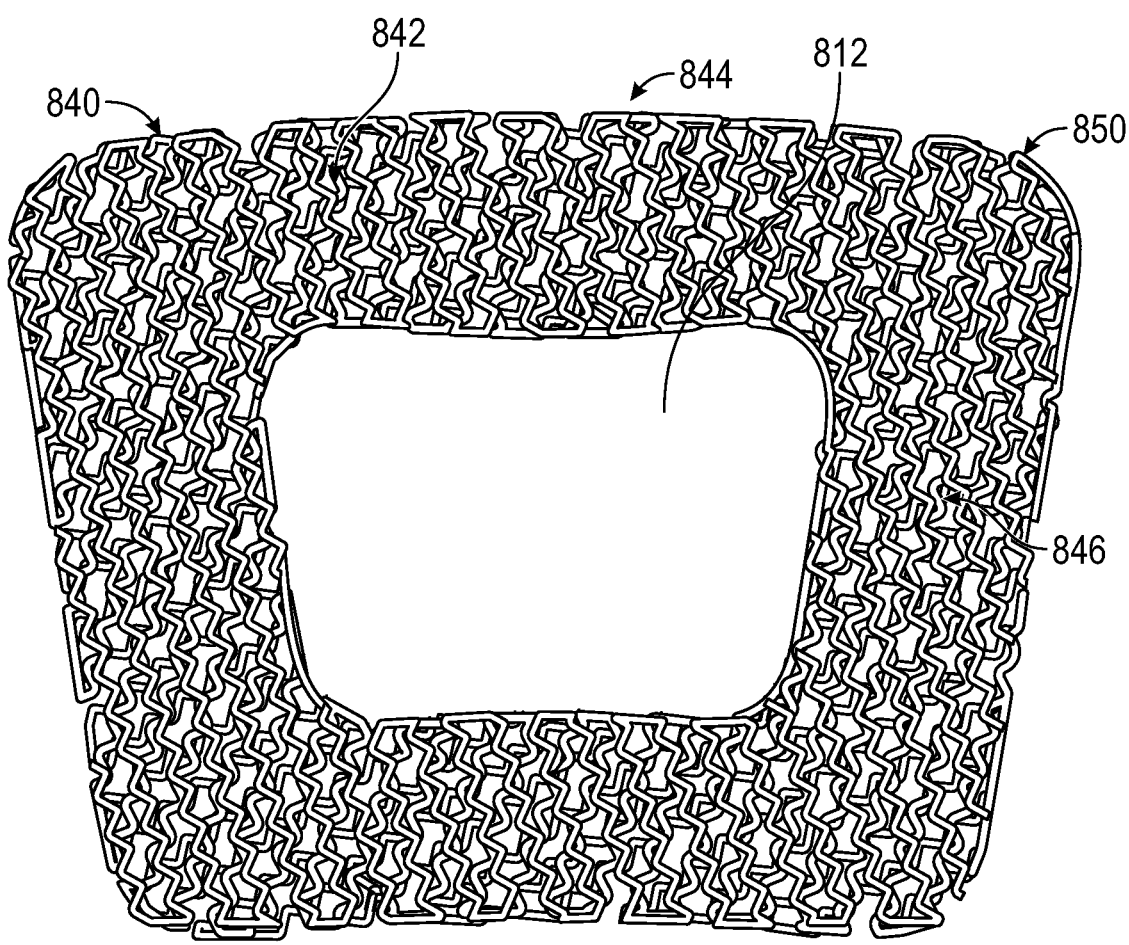
FIG. 8C is a perspective view of a second layer deposited onto the first layer of the embodiment of FIG. 8B.

FIG. 8C illustrates second layer 850 deposited on top of first layer 840, as illustrated in FIG. 8B. In some embodiments, the G-code or software programming can rotate the layout or orientation of wave pattern 842. For example, in some embodiments, second layer 850 is deposited on top of first layer 840 in wave pattern 842 in the same design as present in first layer 840. However, the pattern can be rotated at a predetermined angle or degree, whereby printing material 400 is not deposited in the exact same layout, and instead, there is a crisscrossing effect of printing material 400 between first layer 840 and second layer 850. For example, FIG. 8C illustrates an embodiment in which the printing pattern is rotated about 36° for printing second layer 850 after first layer 840 is completed. In FIG. 8C, wave pattern 842 in second layer 850 comprises the same design as wave pattern 842 of first layer 840, but due to the pattern rotation, printing material 400 is deposited in a resultant crisscrossing manner.

In some embodiments, the process of rotating the print pattern after completion of a build layer of medical implant 802 can be repeated for all layers. In some embodiments, the pattern may be rotated a different amount at different layers. In some embodiments, the pattern may not be rotated for all layers, but rather may be rotated after a number of successive layers. The pattern may be rotated at any predetermined degree, such as within the range of about 1° to about 179°. In some embodiments, the pattern will be rotated at the chosen degree after completion of each layer that is printed. For example, in some embodiments after each layer is completed the pattern will rotate 36° degrees. Furthermore, while the pattern is rotated by control system 50 via the G-code or other software, neither print head 200 nor build plate 100 needs to be physically rotated. The pattern is rotated solely within the software programming, modifying the angle or direction with which the pattern is dispensed. While build plate 100 and print head 200 may be configured to be directionally movable, neither is required to be mechanically rotated during the printing process.

Figure 8D:
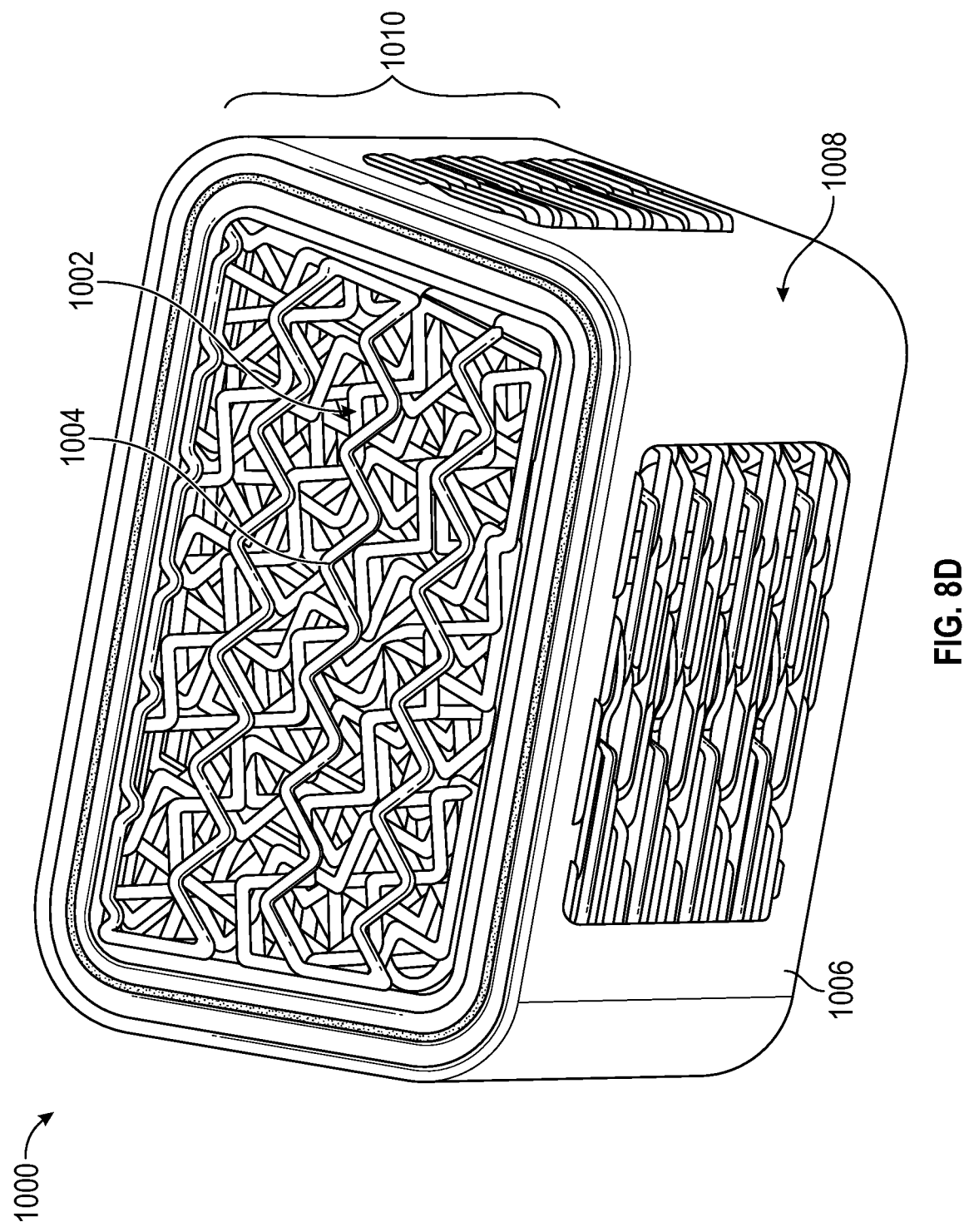
FIG. 8D is a perspective view of an exemplary embodiment of a medical implant that may be printed by printing device of the invention.
Figure 8E:
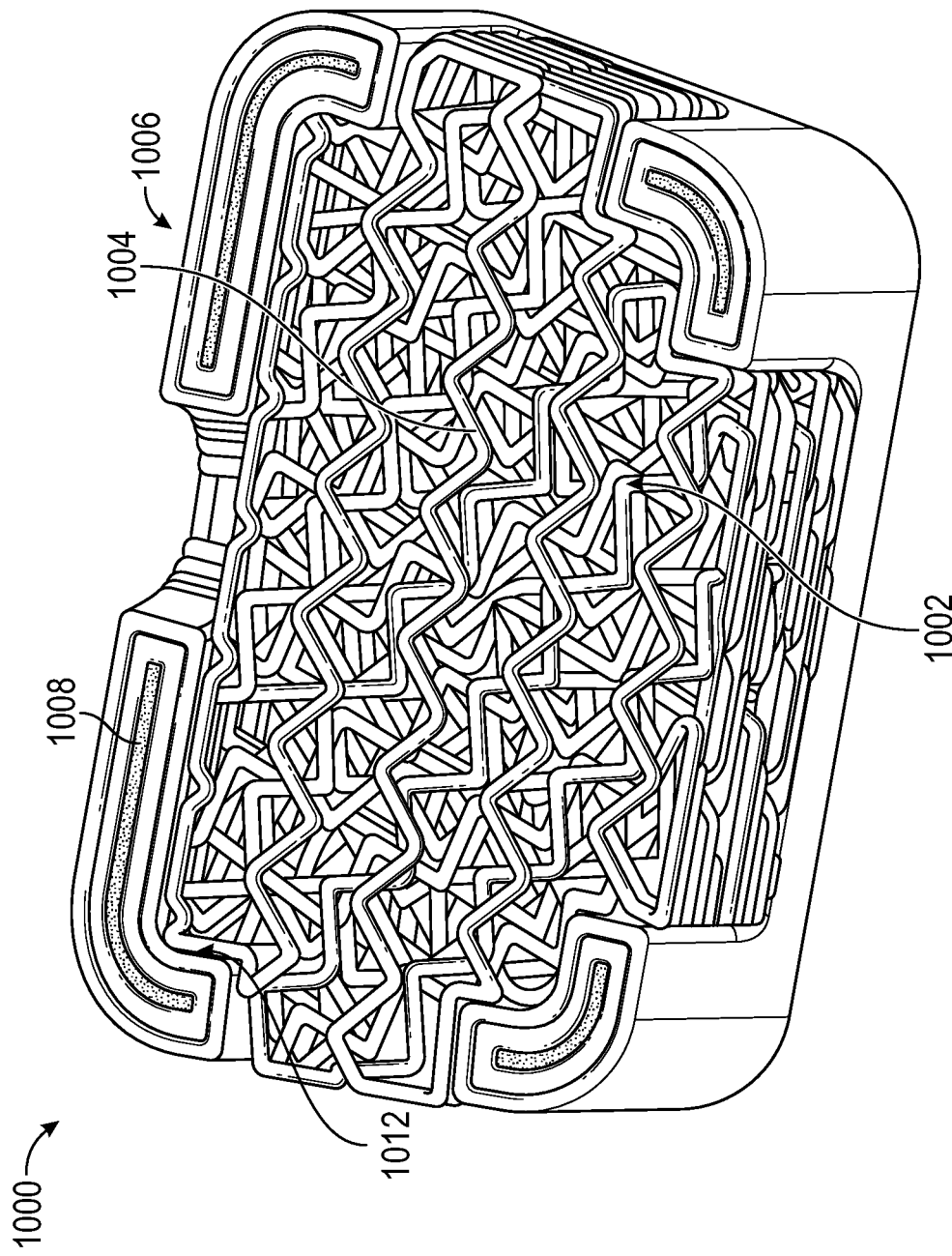
FIG. 8E is a cross-sectional view of the exemplary embodiment of the medical implant of FIG. 8D.

FIG. 8D illustrates an exemplary embodiment of a medical implant 1000, detailing a first porous region 1002 and a second porous region 1006. FIG. 8E illustrates a cross-section of medical implant 1000. In some embodiments, medical implant 1000 may comprise at least a first porous region 1002 having a first porosity and a second porous region 1006 having a second porosity. In some embodiments, medical implant 1000 may comprise more or less than two porous regions and may comprise any number of porous regions having various porosity. In some embodiments, medical implant 1000 may comprise a plurality of layers 1010. In some embodiments, medical implant 1000 may be printed layer-by-layer, wherein the entirety of one layer is printed prior to starting printing of the next layer. This process can be repeated until each layer has been printed and medical implant 1000 is completely formed. In some embodiments, each layer within the plurality of layers 1010 can comprise a first porous region 1002 and a second porous region 1006.

As illustrated in FIGS. 8D-E, in some embodiments, first porous region 1002 may comprise a lattice framework or structure 1004 or otherwise comprise a general structure having defined openings, holes, or spacing throughout the entirety of first porous region 1002. In some embodiments, the lattice framework 1004 comprising first porous region 1002 may comprise pores of about 300 mm to about 350 mm. In some embodiments, first porous region 1002 may comprise pores of about 50 mm to about 500 mm in size. In some embodiments, first porous region 1002 may comprise pores of varying and non-uniform sizes.

As further illustrated in FIGS. 8D-8E, in some embodiments second porous region 1006 may comprise a substantially solid structure 1008, having minimal pores, openings, or gaps. Second porous region 1006 may be printed with the same printing material 400 as first porous region 1002 or may be printed using a different printing material. In some embodiments, second porous region 1006 may comprise a density having minimal or no pores, openings, or gaps. In some embodiments, second porous region 1006 may be formed or printed using an alternative or different pattern than first porous region 1002. For example, in some embodiments second porous region 1006 may be printed using a solid bead of printing material laid in a seam-to-seam manner, resulting in a substantially or completely solid structure. In some embodiments, second porous region 1006 may act as a structural support, aiding in maintaining the structural stability of medical implant 1000.

In some embodiments, the porosity of first porous region 1002 and second porous region 1006 can be predetermined and selectively positioned. For example, in some embodiments medical implant 1000 is a custom, surgical implant designed to be anatomically compatible with a specific patient. Accordingly, it may be advantageous to selectively position a first porous region 1002 in a certain design, shape, configuration, or location that will promote bone growth. Additionally, second porous region 1006 may also be selectively positioned, ensuring that it is positioned in a location and comprises a porosity that supports any load bearing on medical implant 1000.

As described above, the thickness of the bead of dispensed printing material 400 can be dependent on the flow rate of printing material 400 from print head 200. Generally, when printing material 400 is dispensed at a faster rate, the bead will be thinner in diameter than when printing material 400 is dispensed at a slower rate. Accordingly, in some embodiments the flow rate can be selectively programmed or controlled to correspond to the predetermined porosity of sections of object 1000. For example, in some embodiments, the printed material 400 in first porous region 1002 may have a predetermined diameter of about 300 nm to about 350 nm. When dispensing material that will comprise first porous region 1002, printing material 400 may be dispensed at a flow rate of about 10 mm/second. In some embodiments, the printed material 400 in second porous region 1006 may have a predetermined diameter of about 500 nm to about 700 nm. When dispensing material that will comprise second porous region 1006, printing material may be dispensed at a flow rate of about 5 mm/second.

As further illustrated in FIG. 8E, in some embodiments, medical implant 1000 may further comprise at least one overlap area 1012 where first porous region 1002 and second porous region 1006 can interconnect. For example, during the printing process, when printing material 400 is dispensed to print first porous region 1002, printing material 400 may intentionally extend beyond the boundary of first porous region 1002 into the boundary of second porous region 1006. Accordingly, as each layer of medical implant 1000 is printed, overlap area 1012 can also comprise a plurality of interconnected layers, wherein first porous region 1002 and second porous region 1006 continuously interconnect. Overlap area 1012 and the interconnection of first porous region 1002 with second porous region 1006 may result in a more structurally stable medical implant 1000. For example, after the printing process has been completed, and medical implant begins to harden, first porous region 1002 and second porous region 1006 can harden together in an interconnected manner, thereby strengthening the coupling between first porous region 1002 and second porous region 1006.

Using the printing device 10, a user can print an implant 1000 on-site for a patient. Additional embodiments of objects to be printed are described with respect to FIGS. 10, 11, 12 and 13A-E. Specifically, exemplary medical implants 2000, 3000, 4000 are described below.

Figure 10:
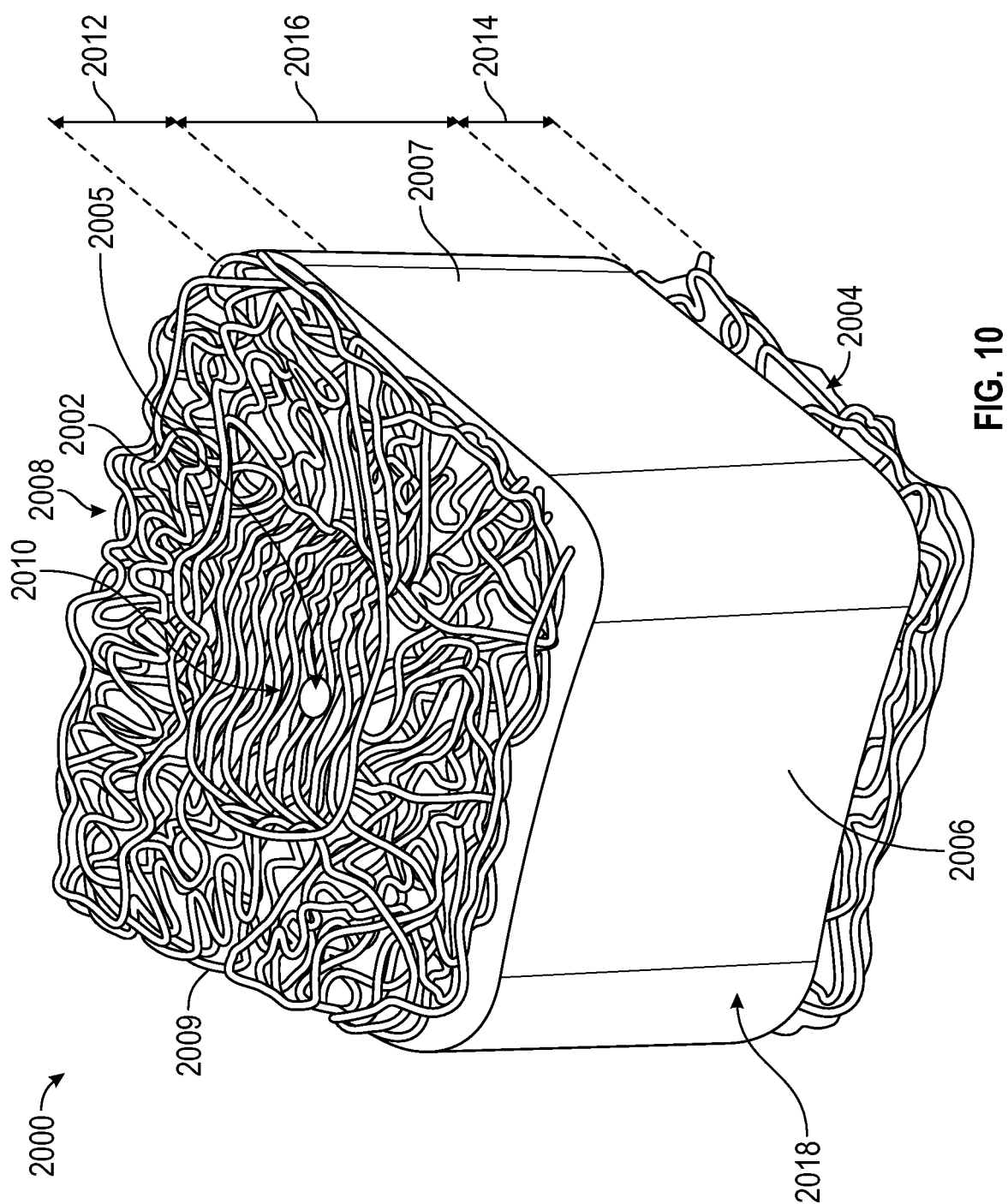
FIG. 10 is a perspective view of an exemplary anterior cervical interbody cage for anterior cervical interbody fusion (ACIF) surgery that may be printed by printing device of the invention.

FIG. 10 shows an anterior cervical interbody cage 2000 that can be printed using the printing device 10. A cervical interbody cage 2000 is designed to support cervical loads while maximizing the surface area between the implant and the vertebral bodies it is in contact with. Cervical interbody cage 2000 is configured to be placed between a first vertebral body and a second vertebral body in a spinal disc space in an anterior cervical interbody fusion (ACIF) procedure. Cervical interbody cage 2000 has a top surface 2002, a bottom surface 2004, an anterior side 2008, a posterior side 2006, and peripheral sides 2007 and 2009. Cervical interbody cage 2000 may include a central opening 2010 that extends from the top surface 2002 to the bottom surface 2004. In some embodiments, the central opening 2010 may be substantially rectangular, square, circular, oval, or any other desired shape. The central opening 2010 may be configured to receive bone graft material therein for stimulating bone growth in situ.

In some embodiments, the top surface 2002 may be slanted at an angle of about 0-30 degrees, angled from anterior side 2008 towards posterior side 2006. In some embodiments, the bottom surface 2004 may be slanted at an angle of about 0-30 degrees, angled from anterior side 2008 towards posterior side 2006. In some embodiments, cervical interbody cage 2000 has a width of about 12-20 mm and a length of about 11-15 mm, and a height of about 5-14 mm.

In some embodiments, the anterior side 2008 may include one or more peripheral openings 2005 therein for receiving a distal end of an instrument for implantation. In some embodiments, one or more peripheral openings 2005 may be internally threaded to cooperate with a distal end of an instrument. In some embodiments, one or more peripheral openings 2005 may be circular. In some embodiments, peripheral sides 2007 and/or 2009 may have openings (not shown) that act as graft windows. However, due to the porous structure of the cervical interbody cage 2000, graft windows in the peripheral sides 2007, 2009 may be unnecessary. In some embodiments, the peripheral openings, or any other openings, may be added after the cervical interbody cage 2000 is printed.

Cervical interbody cage 2000 may be designed to have a plurality of different porous regions. The porosity may be carefully balanced to provide for structural integrity while also providing for optimal bone fixation. For example, the top surface 2002 and the bottom surface 2004 may have the greatest porosity in the implant 2000. In some embodiments, the top surface 2002 and the bottom surface 2004 may have pores of about 300-350 µm. A first region of porosity 2012 may extend down from the top surface 2002 about 1-1.5 mm into the implant 2000. A second region of porosity 2014 may extend up from the bottom surface 2004 about 1-1.5 mm into the implant 2000. It has been found that bony ingrowth may generally extend into an implant about 1-1.5 mm from the adjacent bone surface. A third region of porosity 2016 may extend into the center of the implant 2000 between the first region 2012 and the second region 2014. In some embodiments, a fourth region of porosity 2018 may extend around a periphery of the implant, forming a less porous outer peripheral surface, as seen in FIG. 10. In some embodiments, the fourth region 2018 may have such a small porosity such that it appears solid or almost solid.

Figure 11:
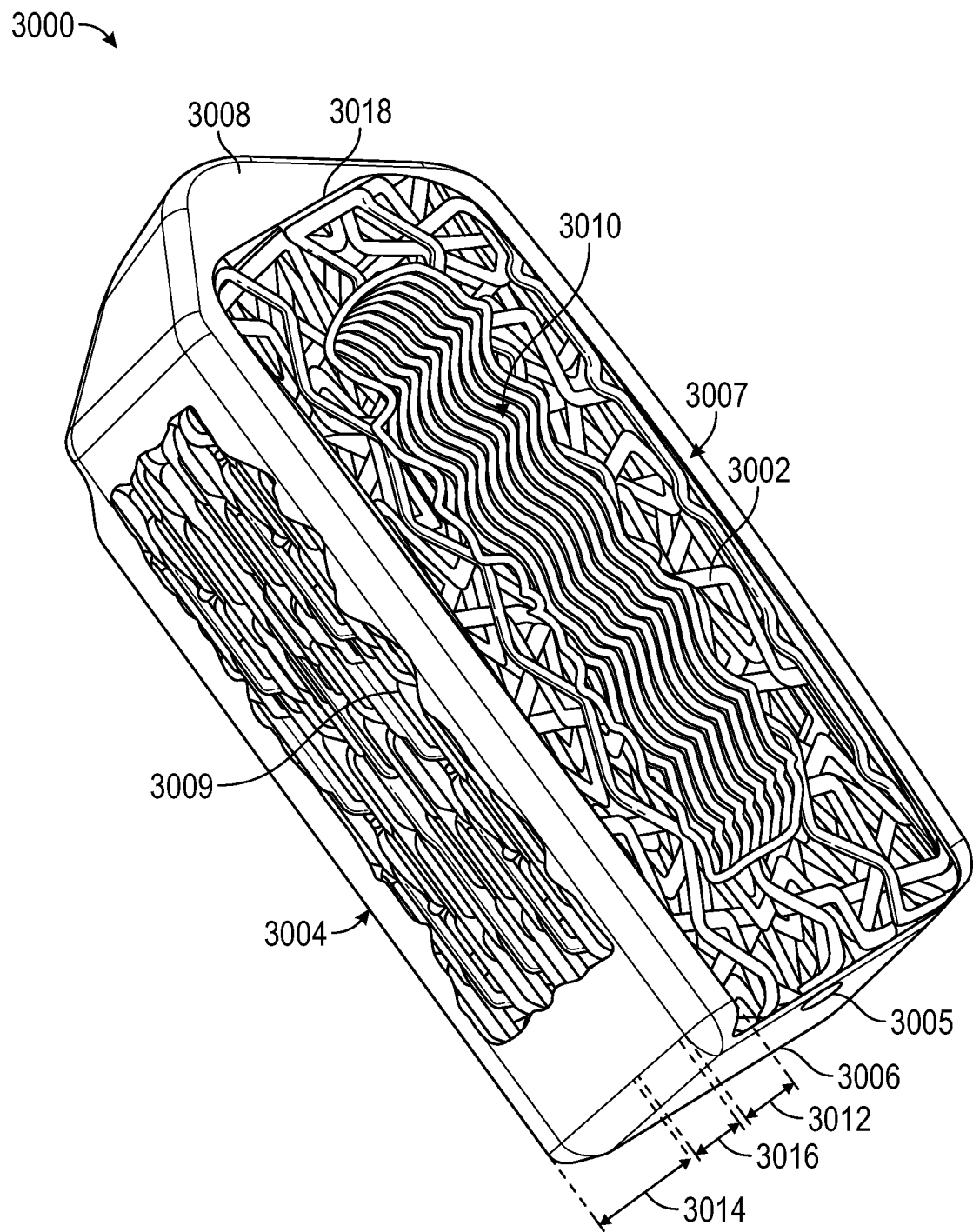
FIG. 11 is a perspective view of an exemplary lumbar spine cage for posterior lumbar interbody fusion (PLIF) surgery that may be printed by printing device of the invention.

FIG. 11 shows an exemplary lumbar spine cage 3000 that can be printed using the printing device 10. A lumbar spinal cage 3000 is designed to support lumbar loads while maximizing the surface area between the implant and the vertebral bodies it is in contact with. Lumbar spinal cage 3000 is configured to be placed between a first vertebral body and a second vertebral body in a spinal disc space in a posterior lumbar interbody fusion (PLIF) procedure. In one embodiment, first vertebral body may be L4 and second vertebral body may be L5. In another embodiment, first vertebral body may be L5 and second vertebral body may be S1. In some embodiments, two lumbar spinal cages 3000 may be implanted in the same disc space.

Lumbar spinal cage 3000 has a top surface 3002, a bottom surface 3004, an anterior side 3008, a posterior side 3006, and peripheral sides 3007 and 3009. Lumbar spinal cage 3000 may include a central opening 3010 that extends from the top surface 3002 to the bottom surface 3004. In some embodiments, the central opening 3010 may be substantially rectangular, square, circular, oval, or any other desired shape. The central opening 3010 may be configured to receive bone graft material therein for stimulating bone growth in situ.

In some embodiments, lumbar spinal cage 3000 may be substantially rectangularly shaped. In some embodiments, anterior side 3008 and posterior side 3006 are shorter, and peripheral sides 3007, 3009 are longer. In such embodiments, central opening 3010 may also be substantially rectangularly shaped. In some embodiments, top surface 3002 and/or bottom surface 3004 may be substantially planar. In some embodiments, top surface 3002 and/or bottom surface 3004 may be substantially convex such that the center has a slightly larger height for engaging the adjacent bones. In some embodiments, lumbar spinal cage 3000 has a width of about 8-12 mm and a length of about 20-40 mm, and a height of about 6-16 mm.

In some embodiments, anterior side 3008 may be shaped to have a substantially triangular-shaped bulleted tip. In some embodiments, the posterior side 3006 may include one or more peripheral openings 3005 therein for receiving a distal end of an instrument for implantation. In some embodiments, one or more peripheral openings 3005 may be internally threaded to cooperate with a distal end of an instrument. In some embodiments, one or more peripheral openings may be circular. In some embodiments, peripheral sides 3007 and/or 3009 may have openings (not shown) that act as graft windows. However, due to the porous structure of the lumbar spinal cage 3000, graft windows in the peripheral sides 3007, 3009 may be unnecessary. In some embodiments, the peripheral openings, or any other openings, may be added after the lumbar spinal cage 3000 is printed.

Lumbar spinal cage 3000 may be designed to have a plurality of different porous regions. The porosity may be carefully balanced to provide for structural integrity while also providing for optimal bone fixation. For example, the top surface 3002 and the bottom surface 3004 may have the greatest porosity in the implant 3000. In some embodiments, the top surface 3002 and the bottom surface 3004 may have pores of about 100-500 µm. A first region of porosity 3012 may extend down from the top surface 3002 about 1-1.5 mm into the implant 3000. A second region of porosity 3014 may extend up from the bottom surface 3004 about 1-1.5 mm into the implant 3000. It has been found that bony ingrowth may generally extend into an implant about 1-1.5 mm from the adjacent bone surface. A third region of porosity 3016 may extend into the center of the implant 3000 between the first region 3012 and the second region 3014. In some embodiments, a fourth region of porosity 3018 may extend around at least a portion of the periphery of the implant, forming a less porous outer peripheral surface. In some embodiments, the fourth region 3018 may have such a small porosity such that it appears solid or almost solid. In some embodiments, the fourth region is primarily on the anterior side 3008 and the posterior side 3006, as seen in FIG. 11.

Figure 12:
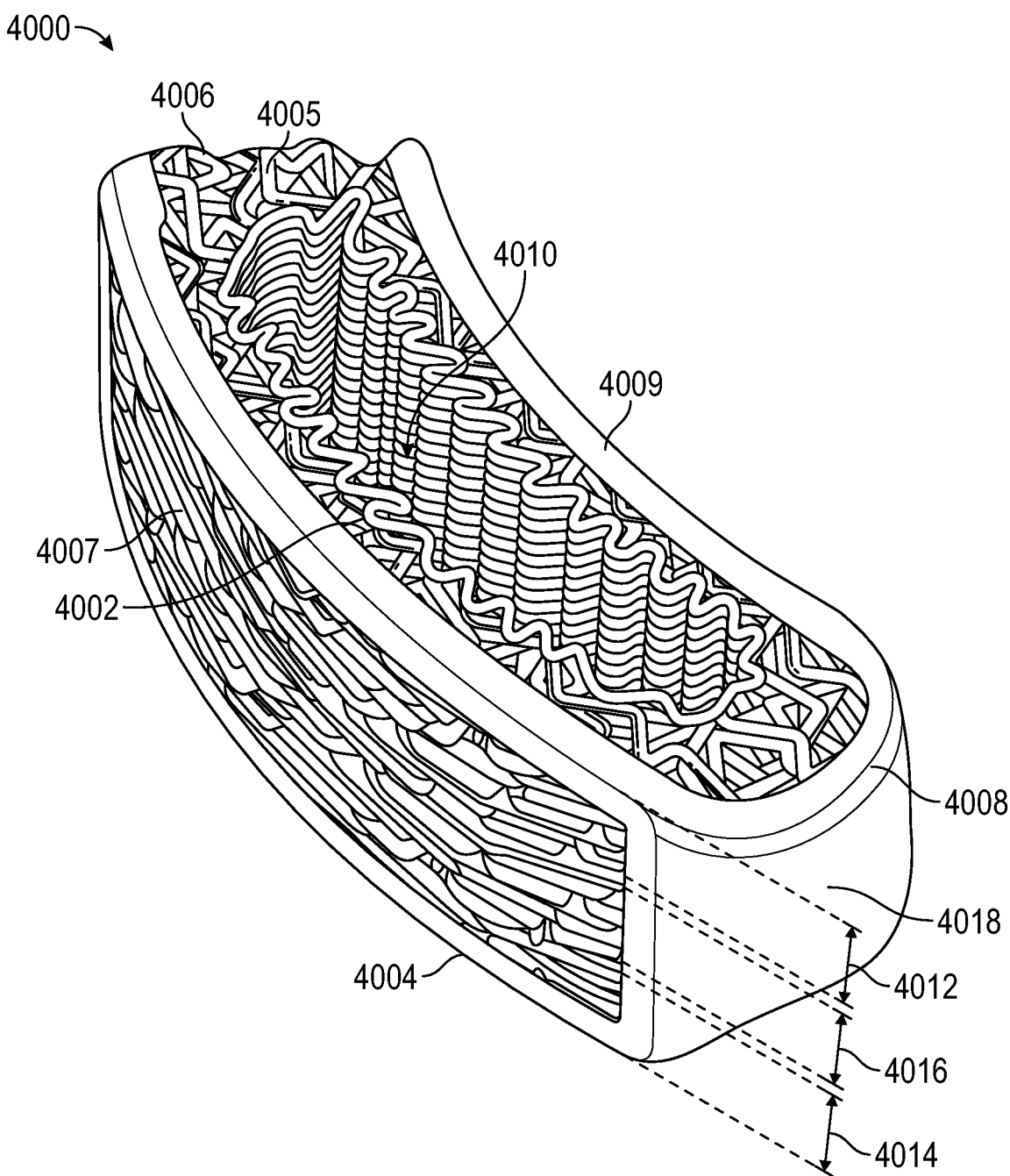
FIG. 12 is a perspective view of an exemplary lumbar spine cage for transforaminal lumbar interbody fusion (TLIF) surgery that may be printed by printing device of the invention.
Figure 13A:
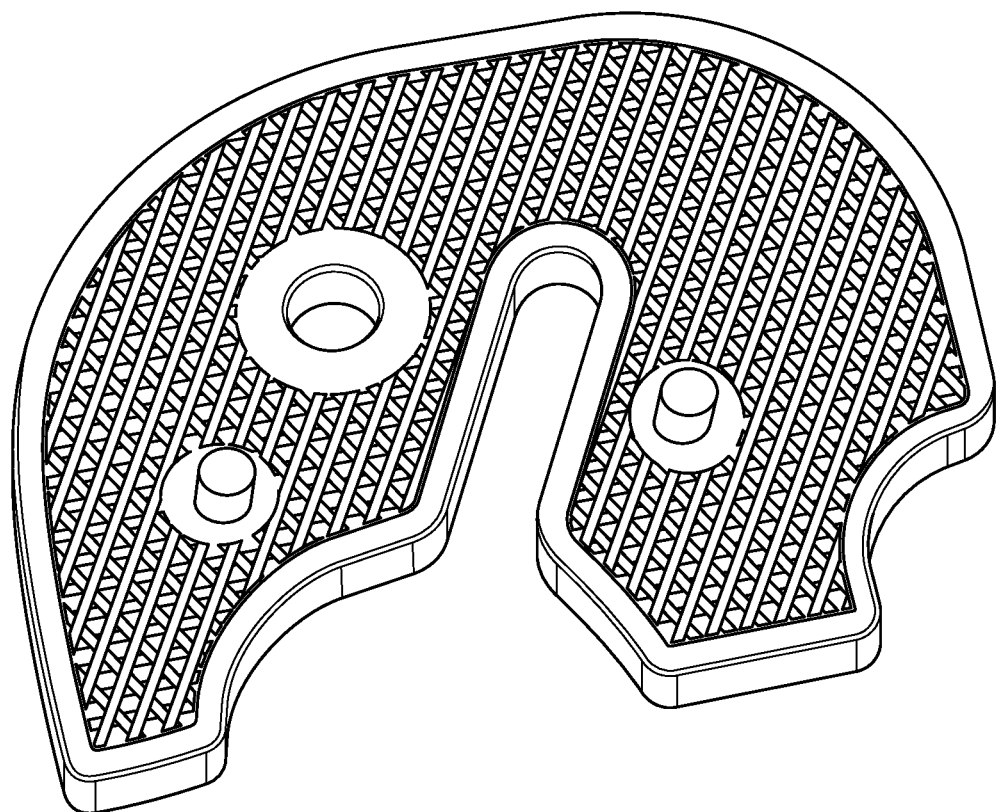
FIG. 13A-E are exemplary embodiments of additional medical implants that may be printed by printing device of the invention.
Figure 13B:
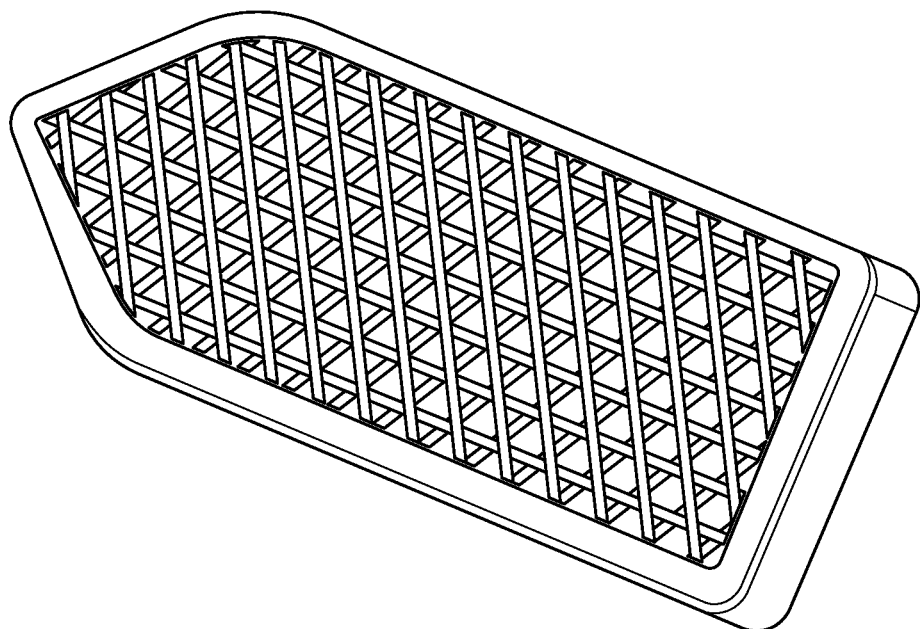
Figure 13C:
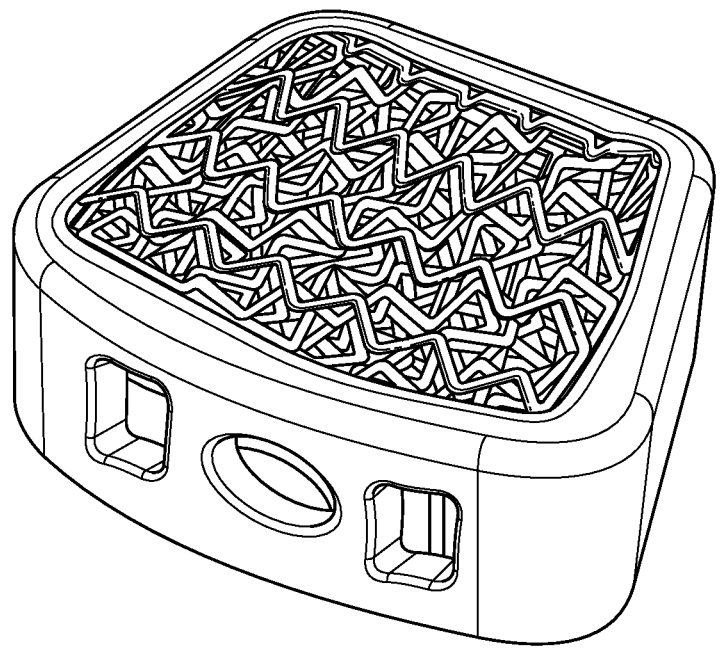
Figure 13D:
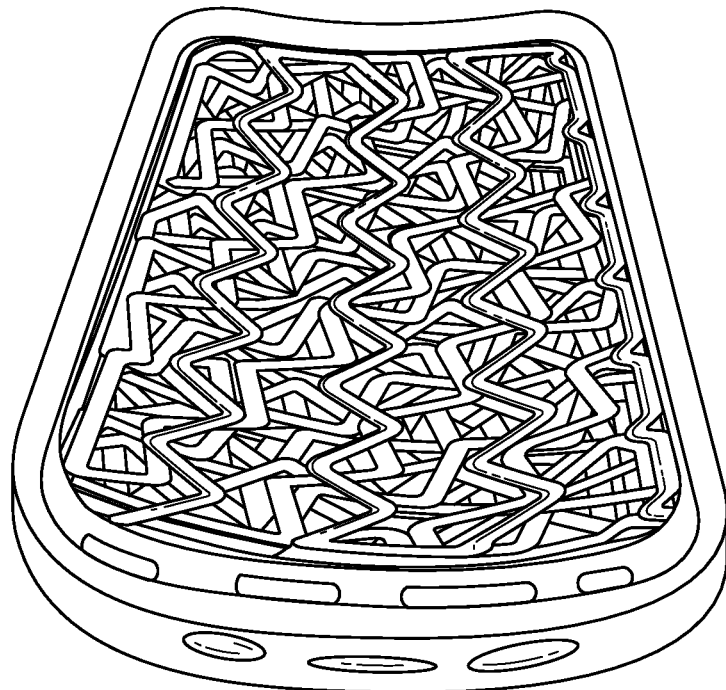
Figure 13E:

FIG. 12 shows an exemplary lumbar spine cage 4000 that can be printed using the printing device 10. A lumbar spinal cage 4000 is designed to support lumbar loads while maximizing the surface area between the implant and the vertebral bodies it is in contact with. Lumbar spinal cage 4000 is configured to be placed between a first vertebral body and a second vertebral body in a spinal disc space in a transforaminal lumbar interbody fusion (TLIF) procedure. In one embodiment, first vertebral body may be L4 and second vertebral body may be L5. In another embodiment, first vertebral body may be L5 and second vertebral body may be S1. In some embodiments, one lumbar spinal cage 4000 is implanted in the intervertebral space.

Lumbar spinal cage 4000 has a top surface 4002, a bottom surface 4004, an anterior side 4008, a posterior side 4006, and peripheral sides 4007 and 4009. Lumbar spinal cage 4000 may include a central opening 4010 that extends from the top surface 4002 to the bottom surface 4004. In some embodiments, the central opening 4010 may be substantially rectangular, square, circular, oval, or any other desired shape. The central opening 4010 may be configured to receive bone graft material therein for stimulating bone growth in situ.

In some embodiments, lumbar spinal cage 4000 may form a substantially curved rectangular shape. In some embodiments, anterior side 4008 and posterior side 4006 are shorter, and peripheral sides 4007, 4009 are longer. In such embodiments, central opening 4010 may be substantially curved and substantially rectangularly shaped. In some embodiments, top surface 4002 and/or bottom surface 4004 may be substantially planar. In some embodiments, top surface 4002 and/or bottom surface 4004 may be substantially convex such that the center has a slightly larger height for engaging the adjacent bones. In some embodiments, lumbar spinal cage 4000 has a width of about 8-14 mm and a length of about 28-34 mm, and a height of about 6-16 mm.

In some embodiments, anterior side 4008 may be shaped to have a substantially triangular-shaped bulleted tip. In some embodiments, the posterior side 4006 may include one or more peripheral openings 4005 therein for receiving a distal end of an instrument for implantation. In some embodiments, one or more peripheral openings 4005 may be internally threaded to cooperate with a distal end of an instrument. In some embodiments, one or more peripheral openings may be circular. In some embodiments, peripheral sides 4007 and/or 4009 may have openings (not shown) that act as graft windows. However, due to the porous structure of the lumbar spinal cage 3000, graft windows in the peripheral sides 4007, 4009 may be unnecessary. In some embodiments, the peripheral openings, or any other openings, may be added after the lumbar spinal cage 4000 is printed.

Lumbar spinal cage 4000 may be designed to have a plurality of different porous regions. The porosity may be carefully balanced to provide for structural integrity while also providing for optimal bone fixation. For example, the top surface 4002 and the bottom surface 4004 may have the greatest porosity in the implant 4000. In some embodiments, the top surface 4002 and the bottom surface 4004 may have pores of about 100-500 μm. A first region of porosity 4012 may extend down from the top surface 4002 about 1-1.5 mm into the implant 3000. A second region of porosity 4014 may extend up from the bottom surface 4004 about 1-1.5 mm into the implant 4000. It has been found that bony ingrowth may generally extend into an implant about 1-1.5 mm from the adjacent bone surface. A third region of porosity 4016 may extend into the center of the implant 4000 between the first region 4012 and the second region 4014. In some embodiments, a fourth region of porosity 4018 may extend around at least a portion of the periphery of the implant, forming a less porous outer peripheral surface. In some embodiments, the fourth region 4018 may have such a small porosity such that it appears solid or almost solid. In some embodiments, the fourth region 4018 is primarily on the anterior side 4008 and the posterior side 4006, as seen in FIG. 12.

In some embodiments, implants 1000, 2000, 3000, or 4000 may include a coating on the outer surfaces thereof. In some embodiments, the coating may include a titanium plasma spray coating and/or a hydroxyapatite (HA) coating. In some embodiments, the coating may be a HA$^{nano}$ Surface® coating, such as manufactured by Promimic. In some embodiments, the coating may be on the outer surfaces and/or may extend into the pores throughout the implant, such as when the implant 1000, 2000, 3000, or 4000 is dipped into a solution for coating.

In some embodiments, the implants 1000, 2000, 3000, or 4000 may include radiopaque markers to optimize visibility and placement. In some embodiments, the radiopaque markers may be tantalum.

In some embodiments, a portion of an implant may be printed on or attached to a secondary material for providing greater structural integrity. Secondary material may be a metal, such as stainless steel or titanium. In some embodiments, the secondary material may form a scaffold for receiving the printing material 400 thereon.

Further to the process as described above, in one embodiment, before printing, a polymeric filament 400 may be dried in a dehydrator overnight. Then the spool 404 having filament 400 thereon is inserted into a material housing 402, and attached to the printing device 10. The polymeric filament 400 is then fed into a transport device 406, which may be a tube running from the housing 402 to the print head 200. The nozzle 210 is heated to the desired melt temperature for the material 400. In some embodiments, the desired melt temperature is about 420° C. to about 450° C. In order to purge the line, about 50 mm of material 400 may be extruded to provide a consistent flow. The build plate 100 is then heated to the desired temperature. In some embodiments, the build plate 100 temperature is about 140° C. to about 160° C. A program is then selected and the object 800 is printed, as described above. After the printing is completed, the raft 816 is removed from the build plate 100. Then the implant 802 is removed from the raft 816 and the scaffolding 818. A knife may be used to remove any excess material.

FIGS. 13A-E shows additional exemplary embodiments of implants that may be printed. Implants may be printed for use in a patient, such as in the spine, an extremity, or the skull. Exemplary implants may be cranial plates, maxillofacial implants, osteotomy wedges, spinal spacers or cages, or screws or fasteners.

In some embodiments, after printing an annealing process is then conducted. Annealing of the polymeric material is done to relieve the internal stresses introduced during fabrication. The polymeric material is heated to a temperature that is below the glass transition temperature such that the polymer chains are excited and realign. For example, the implant 1000, 2000, 3000, or 4000 may be placed in the oven for about 6 hours. In some embodiments, the annealing process may ramp up for the first hour to a temperature of about 150° C., remain at this temperature for about 1 hour, ramp up to about 200° C. over about 30 minutes, remain at about 200° C. for about 1 hour, decrease to about 150° C. over about 30 minutes, remain at about 150° C. for about 30 minutes, and decrease to room temperature (about 20° C.). In some embodiments, the annealing process may be done at a higher temperature, such as about 300° C. when larger printed structures are involved.

In some embodiments, the implant 1000, 2000, 3000, or 4000 is left in the oven overnight so that the implant 1000, 2000, 3000, or 4000 has time to cool to room temperature before being removed. In some embodiments, about fifty implants 1000, 2000, 3000, or 4000 can be placed in the oven at the same time.

The implant 1000, 2000, 3000, or 4000 can then be cleaned. For example, the implant 1000, 2000, 3000, or 400 may be placed in a heated ultrasonic cleaner with a cleaning solution for about 30 minutes. The implant 1000, 2000, 3000, or 4000 may then be placed in an unheated ultrasonic cleaner with a solution of water and isopropyl alcohol.

After the annealing process, any post-machining is done on the implant 1000, 2000, 3000, or 4000. Post-machining may include, for example, adding holes or threading to the implant 1000, 2000, 3000, or 4000. The implant 1000, 2000, 3000, or 4000 may then undergo a cleaning process where any external debris is removed.

The implant 1000, 2000, 3000, or 4000 may be placed in a hyperclean environment for the application of a coating. The implant may be submerged in a hydroxyapatite (HA) solution so that all surfaces are coated with HA. In some embodiments, the coating may be as thin as a nanometer. Due to the fully porous structure of the implant 1000, 2000, 3000, or 4000, the HA coating may extend through the internal porous structure of the device. The use of a HA coating on the implant 1000, 2000, 3000, or 4000 creates a hydrophilic surface and promotes faster osseointegration. The full porosity encourages new bone on-growth and in-growth of the implant leading to greater integration strength. The implant 1000, 2000, 3000, or 4000 may be heated after coating/dipping to evaporate any excess coating material. The implant 1000, 2000, 3000, or 4000 may then be placed in sterile packaging and undergo gamma radiation for sterilization.

Features described above as well as those claimed below may be combined in various ways without departing from the scope thereof. the following examples illustrate some possible, non-limiting combinations:

(A1) A printing device for forming a surgical implant from a first material comprising: a housing forming an enclosed space, a print head, a planar heated build plate having a top surface for receiving the first material thereon, and a reflective plate. The print head comprises a heated nozzle for extruding the first material. The reflective plate comprises an active heating element, said reflective plate is located adjacent to the heated nozzle and has a bottom surface configured to reflect heat towards the build plate. The reflective unit, the heated build plate, and the heated nozzle are all configured to maintain the first material at a predetermined temperature while forming the surgical implant.

(A2) For the printing device denoted as (A1), the heated build plate comprises: a top build layer comprising the top surface; a top frame layer beneath the top build layer; a heating layer comprising a resistant heater beneath the top frame layer; an insulating layer beneath the heating layer; and a bottom frame layer.

(A3) For the printing device denoted as (A2), further comprising an intermediate layer between the heating layer and the top frame layer, wherein the intermediate layer aids in heat dissipation.

(A4) For the printing device denoted as (A2) through (A3), the top layer comprises polyetherimide (PEI), polyetheretherketone (PEEK), polyaryletherketone (PAEK), polyetherketoneketone (PEKK), other thermoplastic polymers, glass, aluminum, stainless steel, other metallic alloys, or combinations thereof.

(A5) For the printing device denoted as any of (A2) through (A4), wherein at least one of the top frame layer and the bottom frame layer comprises aluminum.

(A6) For the printing device denoted as any of (A3) through (A5), wherein the intermediate layer comprises stainless steel.

(A7) For the printing device denoted as any of (A2) through (A6), wherein the insulating layer comprises mica or ceramic.

(A8) For the printing device denoted as any of (A1) through (A7), further comprising at least one infrared heater within the enclosed space configured to direct heat to the surgical implant during printing.

(A9) For the printing device denoted as any of (A1) through (A8), comprising at least one temperature sensor.

(A10) For the printing device denoted as any of (A2) through (A9), further comprising a plurality of openings in the top build layer and the top frame layer, wherein the plurality of openings are configured to receive mechanical couplings therein and to aid in heat dissipation.

(A11) For the printing device denoted as any of (A1) through (A10), further comprising a control system including a processor, configured to receive custom design parameters for forming the surgical implant.

(A12) For the printing device denoted as (A11), the design parameters include size, shape, and porosity.

(A13) For the printing device denoted as any of (A1) through (A12), wherein the first material is a thermoplastic polymer and the predetermined temperature is near the glass transition temperature of the polymer.

(A14) For the printing device denoted as any of (A1) through (A13), wherein an inner surface of the housing comprises a thermally insulating material.

(B1) A system for 3-D printing a medical device comprising: a printing material for forming the medical device and a printing device. The printing device comprises a housing forming an enclosed space, a print head comprising a heated nozzle for extruding the printing material, a planar heated build plate having a top surface for receiving the print material thereon, and a reflective plate comprising an active heating element. The reflective plate is located adjacent to the heated nozzle and has a bottom surface configured to reflect heat towards the build plate. The reflective unit, the build plate, and the nozzle are all configured to maintain the printing material at a predetermined temperature while forming the medical device.

(B2) For the system denoted as (B1), the build plate comprises: a top build layer comprising the top surface; a top frame layer beneath the top build layer; a heating layer comprising a resistant heater beneath the top frame layer; an insulating layer beneath the heating layer; and a bottom frame layer.

(B3) For the system denoted as (B1), further comprising an intermediate layer between the heating layer and the top frame layer, wherein the intermediate layer aids in heat dissipation.

(B4) For the system denoted as (B2) through (B3), the top layer comprises polyetherimide (PEI), polyetheretherketone (PEEK), polyaryletherketone (PAEK), polyetherketoneketone (PEKK), other thermoplastic polymers, glass, aluminum, stainless steel, other metallic alloys, or combinations thereof.

(B5) For the system denoted as any of (B2) through (B4), wherein at least one of the top frame layer and the bottom frame layer comprises aluminum.

(B6) For the system denoted as any of (B3) through (B5), wherein the intermediate layer comprises stainless steel.

(B7) For the system denoted as any of (B2) through (B6), wherein the insulating layer comprises mica or ceramic.

(B8) For the system denoted as any of (B1) through (B7), further comprising at least one infrared heater within the enclosed space configured to direct heat to the surgical implant during printing.

(B9) For the system denoted as any of (B1) through (B8), comprising at least one temperature sensor.

(B10) For the system denoted as any of (B2) through (B9), further comprising a plurality of openings in the top build layer and the top frame layer, wherein the plurality of openings are configured to receive mechanical couplings therein and to aid in heat dissipation.

(B11) For the system denoted as any of (B1) through (B10), further comprising a control system including a processor, configured to receive custom design parameters for forming the medical device.

(B12) For the system denoted as (B11), the design parameters include size, shape, and porosity.

(B13) For the system denoted as any of (B1) through (B12), wherein the printing material is a thermoplastic polymer and the predetermined temperature is near the glass transition temperature of the polymer.

(B14) For the system denoted as any of (B1) through (B13), wherein an inner surface of the housing comprises a thermally insulating material.

(C1) A method for using a printing device to create a medical implant, the method comprising: providing a first material for printing the medical implant; providing a printing device; moving the print head and reflective plate vertically in a Z-plane; and moving the build plate horizontally in a X-plane and in a Y-plane. The printing device comprises a housing forming an enclosed space; a print head comprising a heated nozzle for extruding the first material; a planar heated build plate having a top surface for receiving the first material thereon; and a reflective plate comprising an active heating element. The reflective plate is located adjacent to the heated nozzle and has a bottom surface configured to reflect heat towards the build plate. The reflective unit, the build plate, and the nozzle are all configured to maintain the first material at a predetermined temperature while forming the medical device.

(C2) For the method denoted as (C1), further comprising: providing heat to the build plate to maintain the first material at the predetermined temperature.

(C3) For the method denoted as (C1) or (C2), further comprising: activating the heater in the reflective plate to maintain the first material at the predetermined temperature.

(C4) For the method denoted as any of (C1) through (C3), the printing device further comprises at least one temperature sensor, and the method further comprising: sensing a temperature in at least one location within the housing unit to maintain the first material at the predetermined temperature.

(C5) For the method denoted as (C4), wherein the predetermined temperature is near the glass transition temperature of the first material.

(D1) A method for forming a porous surgical device by contiguous deposition comprising: providing a printing material; extruding the printing material through a nozzle head; moving the nozzle head vertically in a Z-plane; receiving the printing material on a top surface of a build plate; moving the build plate horizontally in a X-plane and in a Y-plane; and depositing a plurality of layers of the printing material on the build plate to form the surgical device. Depositing the plurality of layers comprises (a) depositing a first layer on the build plate; (b) rotating the substantially contiguous pattern by about 36°; and (c) depositing a second layer on top of the first layer; and repeating steps a, b, and c until a predetermined number of layers are formed.

(D2) For the method denoted as (D1) wherein the second layer extends beyond an outer perimeter of the first layer and the second layer.

(D3) For the method denoted as any of (D1) through (D2), further comprising: adjusting a speed at which the printing material is dispensed to control the porosity of the produced surgical device.

(D4) For the method denoted as any of (D1) through (D3), further comprising: heating the printing material at the nozzle to a predetermined temperature, wherein the predetermined temperature is near the glass transition temperature of the printing material.

(D5) For the method denoted as (D4), wherein the predetermined temperature of about 140° C. to about 160° C.

(D6) For the method denoted as any of (D1) through (D5), further comprising: maintaining the predetermined temperature of the printing material on the build plate during the entire process.

(D7) For the method denoted as any of (D1) through (D6), further comprising: customizing the size, shape, and porosity of the implant for a particular patient.

(D8) For the method denoted as any of (D1) through (D7), the printing material comprises polyether-ether-ketone (PEEK), polyaryletherketone (PAEK), polyetherketoneketone (PEKK), or other thermoplastic polymers.

(E1) A method for 3-D printing a medical implant comprising: providing a printing material and a printing device comprising a nozzle; selecting a final shape, size, and configuration of the printed implant; selecting a first porosity for a first region of the implant; selecting a second porosity for a second region of the implant; controlling a dispense rate of the printing material from the nozzle onto a build plate; monitoring a temperature of at least one portion of the printing device by at least one temperature sensor; and adjusting the temperature of at least one element of the printer device to maintain the implant at a predetermined temperature during the entire printing process.

(E2) The method denoted as (E1), further comprising: heating the build plate to maintain the implant at a predetermined temperature.

(E3) The method denoted as (E1) or (E2), wherein the first porosity forms a network of interconnected pores.

(E4) The method denoted as any of (E1) through (E3), wherein the second porosity forms a substantially solid region.

(E5) The method denoted as any of (E1) through (E4), wherein the printing material comprises polyether-ether-ketone (PEEK), polyaryletherketone (PAEK), polyetherketoneketone (PEKK), or other thermoplastic polymers.

(F1) A method for forming a porous surgical device by contiguous deposition comprising: forming a first layer of the surgical device by depositing the printing material on a top surface of a build plate; forming a second layer of the surgical device by depositing the printing material on top of the first layer; and forming the surgical device by continuing to form a plurality of layers relative to the first and second layers. The method may further include forming the first layer by extruding the printing material through the nozzle beginning at a first X-Y position relative to the top surface of the build plate and depositing the printing material in a substantially contiguous pattern to form at least a first region of the porous surgical device, wherein the first region has a first porosity. The method may further include forming the second layer by moving the nozzle in a Z-plane to a second Z-plane position; extruding the printing material through the nozzle beginning at a second X-Y position relative to the top surface of the build plate, wherein the second X-Y position is a predetermined distance or angle from the first X-Y position. The method may further include forming the surgical device by continuing to form a plurality of layers relative to the first and second layers by moving the nozzle in the X-plane relative to a prior Z-plane position, extruding the printing material through the nozzle beginning at an X-Y position relative to the top surface of the build plate, wherein the X-Y position for any one of the plurality of layers is a predetermined distance or angle from any prior X-Y position. Any one of the plurality of layers has a region having a second porosity that is different than a porosity of any prior-formed layer.

(F2) The method denoted as (E1), further comprising: heating the build plate to maintain the device at a predetermined temperature.

(F3) The method denoted as (F1) or (F2), wherein the first porosity forms a network of interconnected pores.

(F4) The method denoted as any of (F1) through (F3), wherein the second porosity forms a substantially solid region.

(F5) The method denoted as any of (F1) through (F4), wherein the printing material comprises polyether-ether-ketone (PEEK), polyaryletherketone (PAEK), polyetherketoneketone (PEKK), or other thermoplastic polymers.

(G1) One or more non-transitory computer-readable media storing computer executable instructions that, when executed by a processor, perform a method of three-dimensionally printing a medical implant, the method comprising: selecting a custom final shape of the implant based at least in part on an anatomy of a particular patient; selecting a first porosity for a first region and selecting a second porosity for a second region of the implant; providing a printing material to a nozzle of a printing device; heating the printing material to at least a melting temperature; and dispensing a plurality of layers of the printing material through the nozzle onto the build plate to form the implant.

(G2) For the media denoted as (G1), further comprising: controlling the nozzle to move vertically in the Z-plane.

(G3) For the media denoted as (G1) or (G2), further comprising: controlling the build plate to move horizontally in a X-plane and/or in a Y-plane.

(G4) For the media denoted as (G1) through (G3), further comprising: dispensing the printing material in a predetermined pattern and after each layer is completed, rotating the pattern by about 36° before printing a successive layer.

(G5) For the media denoted as (G1) through (G4), further comprising: controlling heating of the build plate to maintain the implant at a predetermined temperature during the entire process.

(G6) For the media denoted as (G1) through (G5), wherein the printing material comprises polyether-ether-ketone (PEEK), polyaryletherketone (PAEK), polyetherketoneketone (PEKK), or other thermoplastic polymers.

(G7) For the media denoted as (G1) through (G6), further comprising a memory for storing a library of printable designs for a plurality of different implants.

(H1) A selectively porous customizable medical implant made by the process of fused filament fabrication by a 3-D printer comprising: at least a first region having a first porosity and at least a second region having a second porosity, wherein the pores of the first region are larger than the pores of the second region.

(H2) For the implant as denoted by (H1), the first region has a lattice structure with interconnected pores.

(H3) For the implant as denoted by (H1) or (H2), the implant comprises polyether-ether-ketone (PEEK), polyaryletherketone (PAEK), polyetherketoneketone (PEKK), or other thermoplastic polymers.

(H4) For the implant as denoted by (H1) through (H3), further comprising a hydroxyapatite (HA) coating, wherein the coating extends through the pores.

(H5) For the implant as denoted by (H1) through (H4), the implant is configured to be used as a spinal implant, a cranial flap implant, a maxillofacial implant, or a foot or ankle wedge implant.

(H6) For the selectively porous customizable medical implant as denoted by (H1) through (H5), the pores of the first region have a pore size of about 300 μm.

(I1) A spinal implant formed by a polymer monofilament 3-D printing process, comprising: a top surface; a bottom surface; a peripheral outer surface; and a central opening; and a porous section having a plurality of interconnected pores. The porous section has a first plurality of openings on the top surface and a second plurality of openings on the bottom surface. The implant shape and pore size are selectable for customizing the implant to a particular patient.

(I2) For the spinal implant denoted as (I1), comprising a solid section on the outer peripheral surface.

(I3) For the spinal implant denoted as (I1) or (I2), the porous section comprises a first material, wherein the first material is polyetheretherketone (PEEK), polyaryletherketone (PAEK), polyetherketoneketone (PEKK), or another thermoplastic polymer.

(I4) For the spinal implant denoted as any of (I2) through (I3), the solid section comprises a second material, wherein the second material is titanium, stainless steel, or thermoplastic polymer.

(I5) For the spinal implant denoted as any of (I1) through (I4), the implant is formed by a contiguous deposition of a first material in a plurality of layers.

(I6) For the spinal implant denoted as any of (I1) through (I5), the porous section comprises pores having a size of about 300 μm.

(J1) A surgical implant formed by additive manufacturing comprising: a plurality of layers forming at least one region of interconnected pores, wherein the pores are configured to facilitate bone growth therein. The implant is customizable to the anatomy of a particular patient and is configured for use within the spine, an extremity, or the skull of a patient. The plurality of layers comprise a printing material deposited in a particular predetermined pattern to form the interconnected pores.

(J2) For the surgical implant denoted as (J1) the implant comprises polyetheretherketone (PEEK), polyaryletherketone (PAEK), polyetherketoneketone (PEKK), or another thermoplastic polymer.

(J3) For the surgical implant denoted as (J1) or (J2), comprising a hydroxyapatite (HA) coating extending into the pores.

(J4) For the surgical implant denoted as any of (J1) through (J3), comprising pores having a size of about 300 μm.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method for manufacturing a medical implant, the method comprising:
   providing a first material for printing the medical implant;
   providing a printing device comprising:
      a printing device comprising:
         a housing forming an enclosed space;
         a print head comprising a heated nozzle for extruding the first material;
         a planar heated build plate having a top surface for receiving the first material thereon, wherein the build plate comprises:
            a top build layer comprising the top surface;
            a top frame layer beneath the top build layer;
            a heating layer comprising a resistant heater, said heating layer beneath the top frame layer;
            an insulating layer beneath the heating layer; and
            a bottom frame layer; and
         a reflective plate comprising an active heating element, said reflective plate located adjacent the heated nozzle, said reflective plate having a bottom surface configured to reflect heat towards the build plate;
         wherein the reflective plate, the build plate, and the nozzle are all configured to maintain the first material at a predetermined temperature while forming the medical device;
   moving the print head and the reflective plate vertically in a Z-plane; and
   moving the build plate horizontally in a X-plane and in a Y-plane.

2. The method of claim 1, further comprising:
   providing heat to the build plate to maintain the first material at the predetermined temperature.

3. The method of claim 1, further comprising:
   activating the heating element in the reflective plate to maintain the first material at the predetermined temperature.

4. The method of claim 1, wherein the printing device further comprises at least one temperature sensor, the method further comprising:
   sensing a temperature in at least one location within the housing to maintain the first material at the predetermined temperature.

5. A system for printing a medical device comprising:
a printing material for forming the medical device; and
a printing device comprising:
   a housing forming an enclosed space;
   a print head comprising a heated nozzle for extruding the printing material;
   a planar heated build plate having a top surface for receiving the printing material thereon, wherein the build plate comprises:
     a top build layer comprising the top surface;
     a top frame layer beneath the top build layer;
     a heating layer comprising a resistant heater, said heating layer beneath the top frame layer;
     an insulating layer beneath the heating layer; and
     a bottom frame layer; and
   a reflective plate comprising an active heating element, said reflective plate located adjacent the heated nozzle, said reflective plate having a bottom surface configured to reflect heat towards the build plate,
   wherein the reflective plate, the build plate, and the nozzle are all configured to maintain the printing material at a predetermined temperature while forming the medical device.

6. The system of claim 5, wherein the top build layer comprises polyetherimide (PEI) or polyether-ether-ketone (PEEK), the insulating layer comprises mica or ceramic, and at least one of the bottom frame layer and the top frame layer comprises aluminum.

7. A device for forming a surgical implant from a first material comprising:
   a housing forming an enclosed space;
   a print head comprising a heated nozzle for extruding the first material;
   a planar heated build plate having a top surface for receiving the first material thereon, wherein the heated build plate comprises:
     a top build layer comprising the top surface;
     a top frame layer beneath the top build layer;
     a heating layer comprising a resistant heater, said heating layer beneath the top frame layer;
     an insulating layer beneath the heating layer; and
     a bottom frame layer; and
   a reflective plate comprising an active heating element, said reflective plate located adjacent the heated nozzle, said reflective plate having a bottom surface configured to reflect heat towards the build plate,
   wherein the reflective plate, the heated build plate, and the heated nozzle are all configured to maintain the first material at a predetermined temperature while forming the surgical implant.

8. The device of claim 7, further comprising an intermediate layer between the heating layer and the top frame layer, wherein the intermediate layer aids in heat dissipation.

9. The device of claim 7, wherein the top build layer comprises polyetherimide (PEI), polyether-ether-ketone (PEEK), polyaryletherketone (PAEK), polyetherketoneketone (PEKK), other thermoplastic polymers, glass, aluminum, stainless steel, other metallic alloys, or combinations thereof.

10. The device of claim 7, wherein the insulating layer comprises mica or ceramic.

11. The device of claim 7, wherein at least one of the bottom frame layer and the top frame layer comprise aluminum.

12. The device of claim 7, further comprising at least one infrared heater within the enclosed space configured to direct heat to the surgical implant during printing.

13. The device of claim 7, further comprising at least one temperature sensor.

14. The device of claim 7, further comprising a plurality of openings in the top build layer and the top frame layer, wherein the plurality of openings is configured to receive mechanical couplings therein and to aid in heat dissipation.

15. The device of claim 7, further comprising:
   a control system including a processor configured to receive custom design parameters for forming the surgical implant.

16. The device of claim 15, wherein the design parameters include size, shape, and porosity.

17. The device of claim 7, wherein the first material is a thermoplastic polymer and the predetermined temperature is near a glass transition temperature of the polymer.

18. The device of claim 7, wherein at least one inner surface of the housing comprises a thermally insulating material.

19. The system of claim 5, further comprising a plurality of openings in the top build layer and the top frame layer, wherein the plurality of openings is configured to receive mechanical couplings therein and to aid in heat dissipation.

20. The system of claim 5, further comprising an intermediate layer between the heating layer and the top frame layer, wherein the intermediate layer aids in heat dissipation.

\* \* \* \* \*